United States Patent
Baker et al.

(10) Patent No.: US 8,158,689 B2
(45) Date of Patent: Apr. 17, 2012

(54) HYBRID ABSORBENT FOAM AND ARTICLES CONTAINING IT

(75) Inventors: Andrew T. Baker, Norcross, GA (US); Timothy James Blenke, Neenah, WI (US); Charles W. Colman, Marietta, GA (US); Edward A. Colombo, Penfield, NY (US); Jeffrey E. Fish, Dacula, GA (US); Kaiyuan Yang, Cumming, GA (US); Michael Joseph Garvey, Appleton, WI (US); Jeffrey Jennings Krueger, Marietta, GA (US); Mary Frances Mallory, Alpharetta, GA (US); Joseph E. Pierce, Appleton, WI (US); Fred Robert Radwanski, Stone Mountain, GA (US); Sridhar Ranganathan, Suwanee, GA (US); Donald E. Waldroup, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1539 days.

(21) Appl. No.: 11/315,576

(22) Filed: Dec. 22, 2005

(65) Prior Publication Data

US 2007/0148432 A1 Jun. 28, 2007

(51) Int. Cl.
C08J 9/00 (2006.01)
B32B 3/26 (2006.01)

(52) U.S. Cl. .......................... 521/50; 428/159
(58) Field of Classification Search .................... 521/50; 428/304.4
See application file for complete search history.

(56) References Cited

U.S. PATENT DOCUMENTS

| | | | |
|---|---|---|---|
| 3,432,449 A | 3/1969 | Deal et al. |
| 3,563,243 A | 2/1971 | Lindquist |
| 4,142,956 A | 3/1979 | Shikinami et al. |
| 4,229,396 A | 10/1980 | Suh et al. |
| 4,279,848 A | 7/1981 | Baxter et al. |
| 4,306,035 A | 12/1981 | Baskent et al. |
| 4,318,408 A | 3/1982 | Korpman |
| 4,329,052 A | 5/1982 | Colombo et al. |
| 4,343,911 A | 8/1982 | Hoki et al. |
| 4,384,032 A | 5/1983 | Tashiro et al. |
| 4,394,930 A | 7/1983 | Korpman |
| 4,415,388 A | 11/1983 | Korpman |
| 4,423,110 A | 12/1983 | Sato |

(Continued)

FOREIGN PATENT DOCUMENTS

CA 2129278 2/1995

(Continued)

OTHER PUBLICATIONS

Rynel EPITECH® brochure, 1997.

(Continued)

*Primary Examiner* — Mark Eashoo
*Assistant Examiner* — Peter F Godenschwager
(74) *Attorney, Agent, or Firm* — Armstrong Teasdale LLP

(57) ABSTRACT

A hybrid absorbent foam includes an integrated hybrid foam layer having an open surface, a closed surface, and a foam body extending between the open and closed surfaces. The integrated hybrid foam layer has an open-cell content of at least 50%, while the closed surface provides a barrier to aqueous liquids. The integrated hybrid foam layer is formed as a single layer, and has a substantially uniform polymer composition throughout its thickness. The integrated hybrid foam layer combines the functions of liquid absorbency, retention, and barrier into a single layer, and is useful in a wide variety of absorbent articles.

32 Claims, 12 Drawing Sheets

U.S. PATENT DOCUMENTS

| | | | |
|---|---|---|---|
| 4,435,346 A | 3/1984 | Ito et al. |
| 4,449,977 A | 5/1984 | Korpman |
| 4,519,963 A | 5/1985 | Yoshida et al. |
| 4,554,297 A | 11/1985 | Dabi |
| 4,560,372 A | 12/1985 | Pieniak |
| 4,579,872 A | 4/1986 | Johnson |
| 4,605,682 A | 8/1986 | Park |
| 4,647,593 A | 3/1987 | Bartosiak et al. |
| 4,655,210 A | 4/1987 | Edenbaum et al. |
| 4,676,784 A | 6/1987 | Erdman et al. |
| 4,725,629 A | 2/1988 | Garvey et al. |
| 4,738,810 A | 4/1988 | Cheng-Shiang |
| 4,747,983 A | 5/1988 | Colombo |
| 4,762,860 A | 8/1988 | Park |
| 4,766,157 A | 8/1988 | Yamada et al. |
| 4,867,923 A | 9/1989 | Topcik et al. |
| 4,894,395 A | 1/1990 | Park |
| 4,902,565 A | 2/1990 | Brook |
| 4,918,112 A | 4/1990 | Roox |
| 5,019,062 A | 5/1991 | Ryan et al. |
| 5,110,843 A | 5/1992 | Bries et al. |
| 5,116,662 A | 5/1992 | Morman |
| 5,116,881 A | 5/1992 | Park et al. |
| 5,132,171 A | 7/1992 | Yoshizawa et al. |
| 5,133,917 A | 7/1992 | Jezic et al. |
| 5,147,338 A | 9/1992 | Lang et al. |
| 5,147,345 A | 9/1992 | Young et al. |
| 5,158,986 A | 10/1992 | Cha et al. |
| 5,180,751 A | 1/1993 | Park et al. |
| 5,188,885 A | 2/1993 | Timmons et al. |
| 5,203,764 A | 4/1993 | Libbey et al. |
| 5,204,174 A | 4/1993 | Daponte et al. |
| 5,218,006 A | 6/1993 | Reedy et al. |
| 5,244,931 A | 9/1993 | Kuyzin |
| 5,250,577 A | 10/1993 | Welsh |
| 5,268,224 A | 12/1993 | DesMarais et al. |
| 5,269,987 A | 12/1993 | Reedy et al. |
| 5,277,915 A | 1/1994 | Provonchee et al. |
| 5,286,429 A | 2/1994 | Blythe et al. |
| 5,290,822 A | 3/1994 | Rogers et al. |
| 5,294,482 A | 3/1994 | Gessner |
| 5,302,624 A | 4/1994 | Reedy et al. |
| 5,318,735 A | 6/1994 | Kozulla |
| 5,328,935 A | 7/1994 | Van Phan et al. |
| 5,331,015 A | 7/1994 | DesMarais et al. |
| 5,342,857 A | 8/1994 | Reedy et al. |
| 5,348,795 A | 9/1994 | Park |
| 5,352,711 A | 10/1994 | DesMarais |
| 5,356,944 A | 10/1994 | Blythe et al. |
| 5,366,786 A | 11/1994 | Connor |
| 5,387,207 A | 2/1995 | Dyer et al. |
| 5,389,168 A | 2/1995 | Litchholt et al. |
| 5,403,865 A | 4/1995 | Reedy et al. |
| 5,405,883 A | 4/1995 | Park |
| 5,411,687 A | 5/1995 | Imeokparia et al. |
| 5,433,112 A | 7/1995 | Piche et al. |
| 5,460,818 A | 10/1995 | Park et al. |
| 5,489,407 A | 2/1996 | Suh et al. |
| 5,496,864 A | 3/1996 | Henn et al. |
| 5,534,335 A | 7/1996 | Everhart et al. |
| 5,536,264 A | 7/1996 | Hsueh et al. |
| 5,536,563 A | 7/1996 | Shah et al. |
| 5,550,167 A | 8/1996 | DesMarais |
| 5,567,742 A | 10/1996 | Park |
| 5,573,994 A | 11/1996 | Kabra et al. |
| 5,585,411 A | 12/1996 | Hwo |
| 5,589,519 A | 12/1996 | Knaus |
| 5,595,694 A | 1/1997 | Reedy et al. |
| 5,618,853 A | 4/1997 | Vonken et al. |
| 5,646,194 A | 7/1997 | Kobayashi et al. |
| 5,652,277 A | 7/1997 | Reedy et al. |
| 5,674,916 A | 10/1997 | Shmidt et al. |
| 5,707,571 A | 1/1998 | Reedy |
| 5,728,406 A | 3/1998 | Halberstadt et al. |
| 5,744,506 A | 4/1998 | Goldman et al. |
| 5,763,067 A | 6/1998 | Bruggemann et al. |
| 5,767,189 A | 6/1998 | Palmer, Jr. |
| 5,770,634 A | 6/1998 | Dyer et al. |
| 5,788,889 A | 8/1998 | DeMello et al. |
| 5,795,346 A | 8/1998 | Achter et al. |
| 5,817,261 A | 10/1998 | Reedy et al. |
| 5,849,805 A | 12/1998 | Dyer |
| 5,855,572 A | 1/1999 | Schmidt |
| 5,880,166 A | 3/1999 | Glück et al. |
| 5,883,144 A | 3/1999 | Bambara et al. |
| 5,883,145 A | 3/1999 | Hurley et al. |
| 5,891,814 A | 4/1999 | Richeson et al. |
| 5,905,097 A | 5/1999 | Walther |
| 5,922,780 A | 7/1999 | Dyer et al. |
| 5,929,129 A | 7/1999 | Feichtinger |
| 5,962,543 A | 10/1999 | Kawasaki et al. |
| 5,962,545 A | 10/1999 | Chaudhary et al. |
| 5,993,706 A | 11/1999 | Wilkes et al. |
| 6,008,262 A | 12/1999 | McKay et al. |
| 6,027,795 A | 2/2000 | Kabra et al. |
| 6,030,696 A | 2/2000 | Lee |
| 6,051,174 A | 4/2000 | Park et al. |
| 6,071,580 A | 6/2000 | Bland et al. |
| 6,083,211 A | 7/2000 | DesMarais |
| 6,093,751 A | 7/2000 | Federico et al. |
| 6,093,752 A | 7/2000 | Park et al. |
| 6,096,793 A | 8/2000 | Lee et al. |
| 6,103,358 A | 8/2000 | Brüggemann et al. |
| 6,107,538 A | 8/2000 | Young et al. |
| 6,132,077 A | 10/2000 | Fogarty |
| 6,140,550 A | 10/2000 | Beihoffer et al. |
| 6,156,813 A | 12/2000 | Malwitz et al. |
| 6,174,471 B1 | 1/2001 | Park et al. |
| 6,197,233 B1 | 3/2001 | Mason et al. |
| 6,197,841 B1 | 3/2001 | Takimoto et al. |
| 6,221,928 B1 | 4/2001 | Kozma et al. |
| 6,231,960 B1 | 5/2001 | Dyer et al. |
| 6,235,360 B1 | 5/2001 | Lanzani et al. |
| 6,245,697 B1 | 6/2001 | Conrad et al. |
| 6,258,863 B1 | 7/2001 | Harfmann et al. |
| 6,258,868 B1 | 7/2001 | Heymann |
| 6,261,679 B1 | 7/2001 | Chen et al. |
| 6,262,137 B1 | 7/2001 | Kozma et al. |
| 6,268,046 B1 | 7/2001 | Miller et al. |
| 6,281,289 B1 | 8/2001 | Maugans et al. |
| 6,297,326 B1 | 10/2001 | Wang et al. |
| 6,310,112 B1 | 10/2001 | Vo et al. |
| 6,325,956 B2 | 12/2001 | Chaudhary et al. |
| 6,329,450 B1 | 12/2001 | Ogoe et al. |
| 6,355,341 B1 | 3/2002 | Chaudhary et al. |
| 6,372,953 B1 | 4/2002 | Young et al. |
| 6,376,565 B1 | 4/2002 | Dyer et al. |
| 6,388,014 B1 | 5/2002 | Park et al. |
| 6,391,438 B1 | 5/2002 | Ramesh et al. |
| 6,398,997 B1 | 6/2002 | Ligon, Sr. et al. |
| 6,399,854 B1 | 6/2002 | Vartiainen |
| 6,414,047 B1 | 7/2002 | Abe |
| 6,417,240 B1 | 7/2002 | Park |
| 6,436,521 B1 | 8/2002 | Lee |
| 6,451,865 B1 | 9/2002 | Migchels et al. |
| 6,458,877 B1 | 10/2002 | Ahmed et al. |
| 6,605,332 B2 | 8/2003 | Calhoun et al. |
| 6,638,985 B2 | 10/2003 | Gehlsen et al. |
| 6,653,360 B2 | 11/2003 | Gupta |
| 2002/0010270 A1 | 1/2002 | Czech et al. |
| 2002/0025988 A1 | 2/2002 | Maekawa et al. |
| 2002/0197442 A1 | 12/2002 | Wyner et al. |
| 2003/0065298 A1* | 4/2003 | Krishnaswamy-Mirle et al. ............. 604/378 |
| 2004/0005434 A1 | 1/2004 | Calhoun et al. |
| 2005/0124709 A1 | 6/2005 | Krueger et al. |

FOREIGN PATENT DOCUMENTS

| | | |
|---|---|---|
| CA | 2129278 C * | 5/2002 |
| EP | 0 041 934 | 12/1981 |
| EP | 0 043 052 | 1/1982 |
| EP | 0 228 353 B1 | 5/1991 |
| EP | 0 328 518 B1 | 5/1991 |
| EP | 0 453 286 A2 | 10/1991 |
| EP | 0 475 174 B1 | 5/1996 |
| EP | 0 517 748 B1 | 12/1996 |
| EP | 0 753 529 A2 | 1/1997 |

| | | |
|---|---|---|
| EP | 0 642 907 B1 | 5/1997 |
| EP | 0 585 147 B1 | 4/1998 |
| EP | 0 878 481 A1 | 11/1998 |
| EP | 0 921 148 A1 | 6/1999 |
| EP | 0 674 579 B1 | 6/2000 |
| EP | 0 662 493 B1 | 10/2000 |
| EP | 0 753 529 A3 | 11/2000 |
| EP | 1 048 276 A1 | 11/2000 |
| EP | 1 054 033 A1 | 11/2000 |
| EP | 1 072 367 A1 | 1/2001 |
| EP | 1 115 777 B1 | 7/2001 |
| EP | 0 891 390 B1 | 8/2001 |
| EP | 0 704 476 B1 | 12/2001 |
| EP | 1 182 224 A1 | 2/2002 |
| EP | 1 219 673 A2 | 7/2002 |
| EP | 1 219 673 A3 | 7/2002 |
| EP | 1 079 786 B1 | 8/2002 |
| EP | 0 702 032 B1 | 11/2002 |
| EP | 0 975 696 B1 | 6/2003 |
| GB | 2 259 464 A | 3/1993 |
| GB | 2 279 013 A | 12/1994 |
| JP | 4-46981 | 7/1992 |
| JP | 6-280317 | 10/1994 |
| JP | 2001-342277 | 12/2001 |
| WO | WO 86/00628 | 1/1986 |
| WO | WO 91/08037 | 6/1991 |
| WO | WO 94/13460 | 6/1994 |
| WO | WO 97/07907 | 3/1997 |
| WO | WO 97/11985 | 4/1997 |
| WO | WO 97/31053 | 8/1997 |
| WO | WO 98/10015 | 3/1998 |
| WO | WO 98/14508 | 4/1998 |
| WO | WO 98/16575 | 4/1998 |
| WO | WO 98/37131 | 8/1998 |
| WO | WO 98/41574 | 9/1998 |
| WO | WO 98/58991 | 12/1998 |
| WO | WO 99/00236 | 1/1999 |
| WO | WO 99/29765 | 6/1999 |
| WO | WO 99/47092 | 9/1999 |
| WO | WO 99/47592 | 9/1999 |
| WO | WO 99/52955 | 10/1999 |
| WO | WO 00/15697 | 3/2000 |
| WO | WO 00/15700 | 3/2000 |
| WO | WO 00/53669 | 3/2000 |
| WO | WO 01/09239 A1 | 2/2001 |
| WO | WO 01/15643 A1 | 3/2001 |
| WO | WO 01/16220 A1 | 3/2001 |
| WO | WO 01/21227 A1 | 3/2001 |
| WO | WO 01/27191 A1 | 4/2001 |
| WO | WO 01/34687 A1 | 5/2001 |
| WO | WO 01/40374 A2 | 6/2001 |
| WO | WO 01/40374 A3 | 6/2001 |
| WO | WO 01/64154 A1 | 9/2001 |
| WO | WO 01/70479 A1 | 9/2001 |
| WO | WO 01/70859 A2 | 9/2001 |
| WO | WO 01/70859 A3 | 9/2001 |
| WO | WO 01/70860 A2 | 9/2001 |
| WO | WO 01/70860 A3 | 9/2001 |
| WO | WO 01/80916 A2 | 11/2001 |
| WO | WO 01/80916 A3 | 11/2001 |
| WO | WO 02/07791 A2 | 1/2002 |
| WO | WO 02/07791 A3 | 1/2002 |
| WO | WO 02/12379 A1 | 2/2002 |
| WO | WO 02/14424 A2 | 2/2002 |
| WO | WO 02/18482 A2 | 3/2002 |
| WO | WO 02/22339 A1 | 3/2002 |
| WO | WO 02/34823 A2 | 5/2002 |
| WO | WO 02/068530 A2 | 9/2002 |

OTHER PUBLICATIONS

Jeffrey Csemica and Alisha Brown, "Effect of Plasticizers on the Properties of Polystyrene Films", Journal of Chemical Education, vol. 76, No. 11, Nov. 1999, pp. 1526-1528.

"Kraton D and G Polmers" www.Kraton.com/kraton/generic/menu. asp?ID=220, Oct. 2001.

"Epolene Polymers", www.eastman.com/Brands/Epolene/Epolene_Intro.asp, 2003.

Epolene® Polymers brochure, Eastman Chemical Company, 2002, pp. 9, 11, 12.

"Epolene Polymers," vvww.eastman.com/Online_Publications/F243/f24304.htm, 1994.

"Epolene Polymers: Effective Processing Aids for Rubber," Eastman Chemical Company, Aug. 1995, pp. 1-8.

"Glycerol Monooleate: Processing," National Organic Standards Board Technical Advisory Panel Review, Sep. 2001, pp. 1-16.

Principles of Polymer Systems, Ferdinand Rodriquez, McGraw-Hill Book Co., 1070, pp. 43-46, (2003).

Landrock, *Handbook of Plastic Foams*, William Andrew Publishing (1995), p. 308.

\* cited by examiner

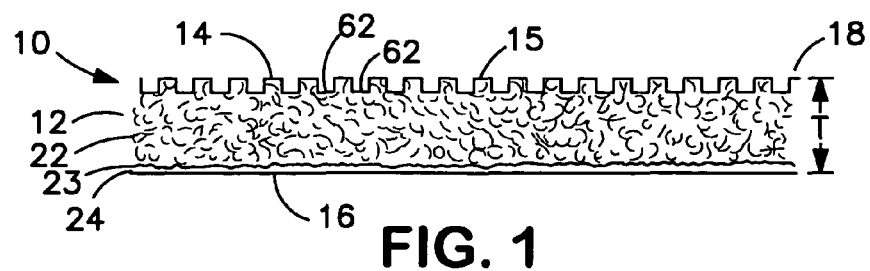
FIG. 1
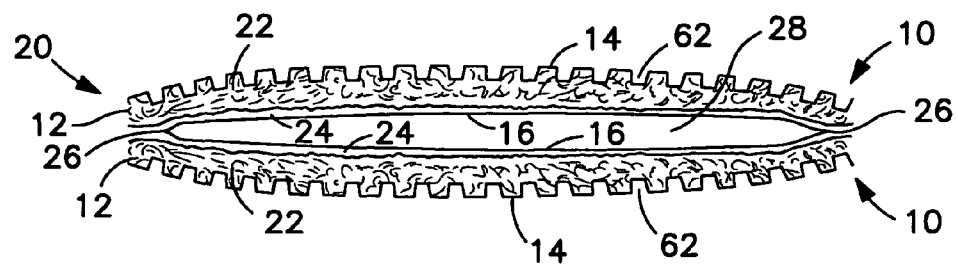
FIG. 2
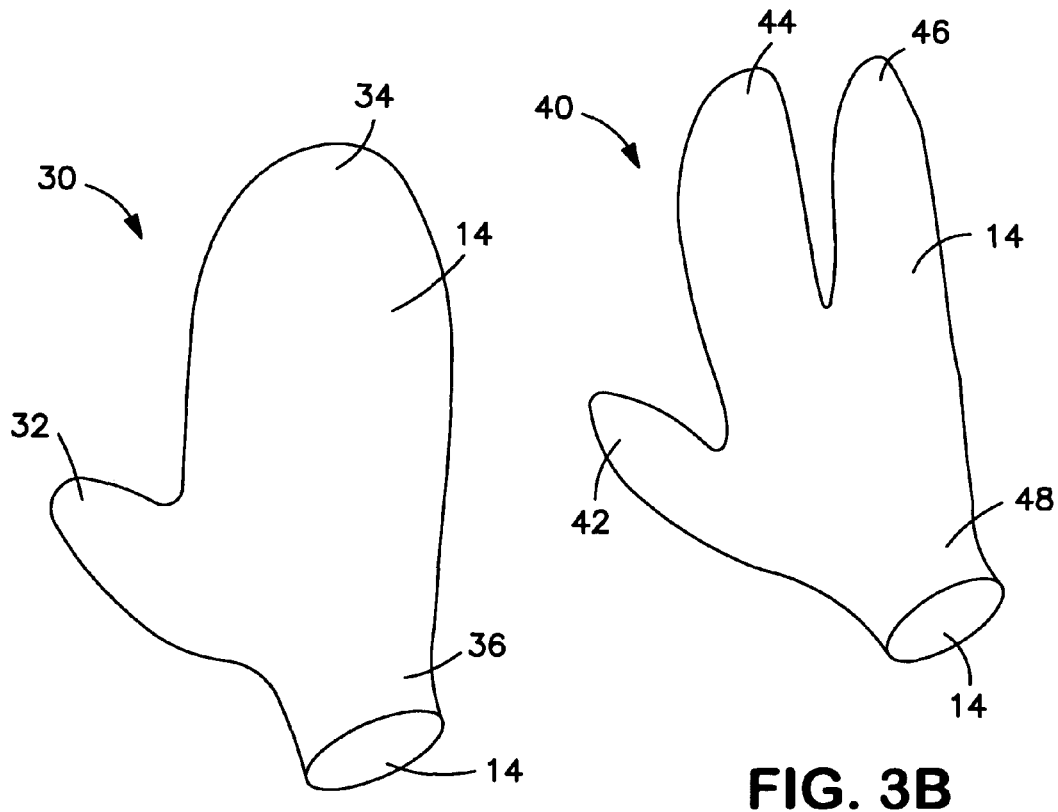
FIG. 3A
FIG. 3B

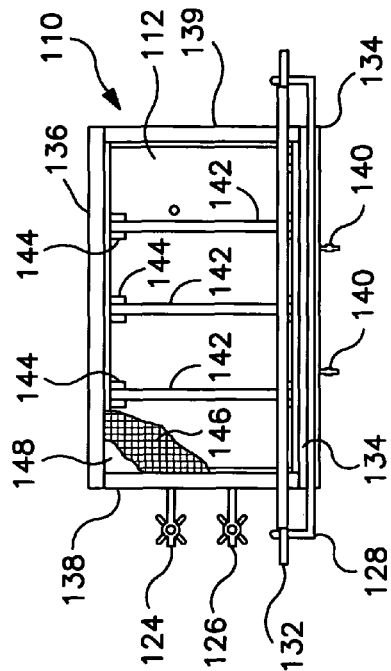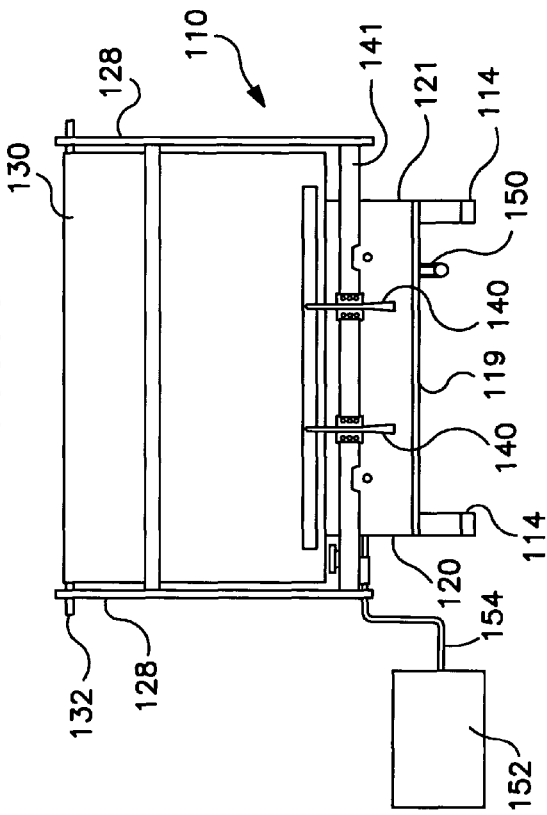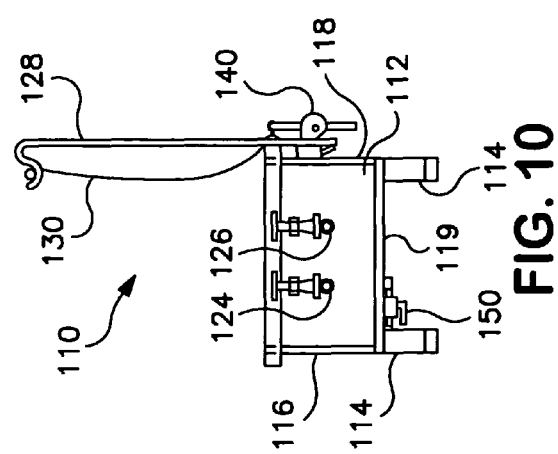

HYBRID ABSORBENT FOAM AND ARTICLES CONTAINING IT

BACKGROUND OF THE INVENTION

Absorbent, open-celled foams are useful in a variety of absorbent garments and other absorbent articles for personal care and medical use. These materials possess dimensional stability, structural integrity, and an ability to spontaneously recover to an original shape when squeezed or folded.

In many such applications, a material combination is needed which receives liquid on one side, and absorbs it, yet which is substantially leak-proof on the opposing side. To this end, open-celled absorbent foams have been laminated to another material, such as a barrier layer, which prevents the expulsion of liquid on one side. A wide variety of suitable barrier materials have been developed which are substantially impermeable to water and aqueous liquids. Some of these materials are breathable to water vapor, to facilitate wearer comfort of an absorbent garment containing the material.

Many absorbent garments and other absorbent articles possess multiple layers which perform different functions. While the multiple layers optimize the performance of the article, the layers typically require separate fabrication, processing and cutting, as well as suitable lamination to each other. In today's cost-cutting environment, there is a need or desire to simplify the manufacture of absorbent articles by providing individual materials which perform multiple functions previously requiring multiple layers.

SUMMARY OF THE INVENTION

The present invention is directed to a hybrid absorbent thermoplastic foam and articles containing it. The hybrid absorbent thermoplastic foam includes an integrated hybrid thermoplastic foam layer having an open surface, a closed surface, and a body having a thickness defined by a distance between the open and closed surfaces. The open surface has an open area of greater than 10%, suitably higher as explained below. The "open area" is the percentage of the surface occupied by openings that extend into an open-cell foam portion of the body, which has an open-cell content of about 50% or greater. The body (which includes the open and closed surfaces and the structure between them) has an overall open-cell content of about 50% or greater. The closed surface provides a barrier to the passage of liquids. The closed portion of the body (defining the closed surface) has a thickness which is small relative to the thickness of the body.

The integrated hybrid foam layer can be extruded as a single layer and, therefore, has a substantially uniform polymer composition throughout the thickness of the body. The integrated hybrid foam layer combines the dual functions of absorbency and liquid barrier into a single manufactured layer. The integrated hybrid foam layer may receive aqueous liquid from the open surface, store it in the body, and retain it in the body due to the liquid barrier function provided by the closed surface.

The present invention is also directed to personal care absorbent articles, medical absorbent articles, and industrial absorbent articles which incorporate the hybrid absorbent foam of the invention. In particular, the invention is directed to absorbent gloves, mitts, and wipes.

With the foregoing in mind, it is a feature and advantage of the invention to provide a hybrid absorbent foam which combines the functions of liquid intake, storage, and barrier into a single integrated hybrid foam layer.

It is also a feature and advantage to provide improved, lower cost absorbent articles which incorporate the hybrid absorbent foam.

BRIEF DESCRIPTION OF THE DRAWINGS

FIG. 1 is a sectional view of an integrated hybrid foam layer.

FIG. 2 is a sectional view of a laminate including two integrated hybrid foam layers joined at their respective edges with their closed surfaces facing each other.

FIGS. 3(a)-3(c) are plan views of a mitt and gloves that can be formed using the laminate of FIG. 2.

FIG. 9 representatively shows a partially cut away top view of a saturated capacity tester.

FIG. 10 representatively shows a side view of a saturated capacity tester.

FIG. 11 representatively shows a rear view of a saturated capacity tester.

In FIG. 17A, the open surface was prepared by raising. In FIG. 18B, the open surface was prepared by sueding and aperturing.

DEFINITIONS

Figure 3C:
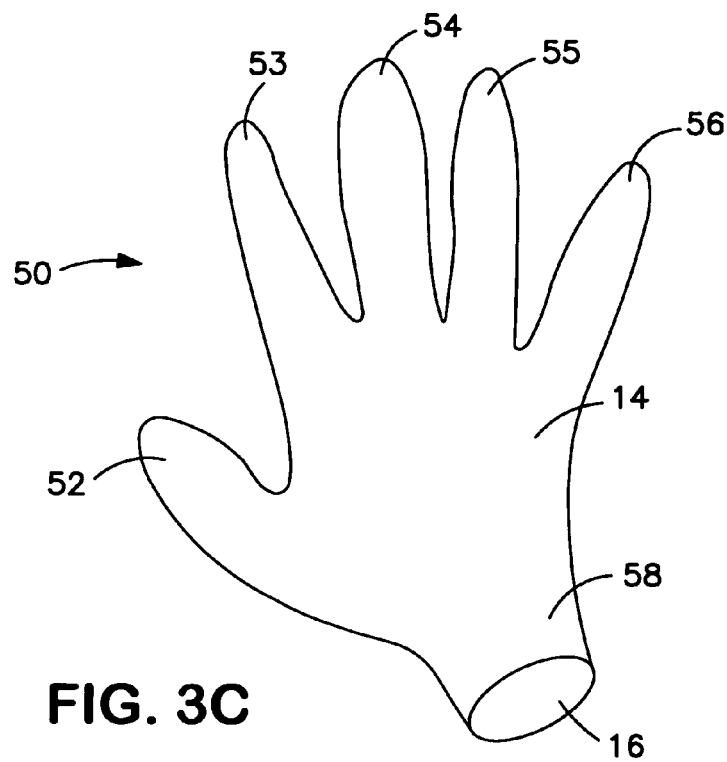

Within the context of this specification, each term or phrase below will include the following meaning or meanings:

"Cell" refers to a cavity contained in foam. A cell is closed when the cell membrane surrounding the cavity or enclosed opening is not perforated and has all membranes intact. Cell connectivity occurs when at least one wall of the cell membrane surrounding the cavity has orifices or pores that connect to adjacent cells, such that an exchange of fluid is possible between adjacent cells.

"Compression" refers to the process or result of pressing by applying force on an object, thereby increasing the density of the object.

"Elastomer" refers to material having elastomeric or rubbery properties. Elastomeric materials, such as thermoplastic elastomers, are generally capable of recovering their shape after deformation when the deforming force is removed. Specifically, as used herein, elastomeric is meant to be that property of any material which upon application of an elongating force, permits that material to be stretchable to a stretched length which is at least about 25 percent greater than its relaxed length, and that will cause the material to recover at least 40 percent of its elongation upon release of the stretching elongating force. A hypothetical example which would satisfy this definition of an elastomeric material in the X-Y planar dimensions would be a one (1) inch (2.54 cm) sample of a material which is elongatable to at least 1.25 inches (3.18 cm) and which, upon being elongated to 1.25 inches (3.18 cm) and released, will recover to a length of not more than 1.15 inches (2.92 cm). Many elastomeric materials may be stretched by much more than 25 percent of their relaxed length, and many of these will recover to substantially their original relaxed length upon release of the stretching, elongating force. In addition to a material being elastomeric in the described X-Y planar dimensions of a structure, including a web or sheet, the material can be elastomeric in the Z planar dimension. Specifically, when a structure is applied compression, it displays elastomeric properties and will essentially recover to its original position upon relaxation. Compression set is sometimes used to describe such elastic recovery.

"Open-cell" refers to any cell that has at least one broken or missing membrane or a hole in a membrane.

"Plasticizing agent" refers to a chemical agent that can be added to a rigid polymer to add flexibility to rigid polymers. Plasticizing agents typically lower the glass transition temperature.

"Polymer" generally includes but is not limited to, homopolymers, copolymers, including block, graft, random and alternating copolymers, terpolymers, etc., and blends and modifications thereof. Furthermore, unless otherwise specifically limited, the term "polymer" shall include all possible molecular geometrical configurations of the material. These configurations include, but are not limited to isotactic, syndiotactic and atactic symmetries.

"Surfactant" refers to a compound, such as a detergent or wetting agent, that affects the surface tension of fluids.

"Thermoplastic" is meant to describe a material that softens and/or flows when exposed to heat and which substantially returns to its original hardened condition when cooled to room temperature.

"Absorbent article" includes, but is not limited to, personal care absorbent articles, medical absorbent articles, absorbent wiping articles, as well as non-personal care absorbent articles including filters, masks, packaging absorbents, trash bags, mitts, gloves, stain removers, topical compositions, laundry soil/ink absorbers, detergent agglomerators, lipophilic fluid separators, cleaning devices, liquid delivery articles, and the like.

"Personal care absorbent article" includes, but is not limited to, absorbent articles such as disposable diapers, baby wipes, training pants, child-care pants, and other disposable garments; feminine-care products including sanitary napkins, wipes, menstrual pads, panty liners, panty shields, interlabials, tampons, and tampon applicators; adult-care products including wipes, pads, containers, incontinence products, and urinary shields, personal gloves, mitts, liquid delivery articles, and the like.

"Medical absorbent article" includes a variety of professional and consumer health-care products including, but not limited to, products for applying hot or cold therapy, hospital gowns, surgical drapes, bandages, wound dressings, covers, containers, filters, disposable garments and bed pads, medical absorbent garments, gowns, underpads, wipes, medical gloves, mitts, liquid delivery articles, and the like.

"Absorbent wiping article" or "wipe" includes facial tissue, towels such as kitchen towels, disposable cutting sheets, away-from-home towels and wipers, wet-wipes, sponges, washcloths, bath tissue, gloves, mitts, liquid delivery articles, and the like.

"Industrial absorbent article" includes sponges, cleaning fluid dispensers, towels, liquid delivery articles, wipes, gloves, mitts, and the like which are useful in industrial cleaning applications and, in some instances, household cleaning applications.

"Open-cell foam" refers to a foam having an open-cell content of at least 50%, measured using ASTM D2856.

"Open area" refers to the percentage of the surface occupied by openings which extend from the surface at least to an open-cell portion of the foam body, measured using the Open Area Test described below.

"Open surface" refers to a foam surface having an open area greater than 10%, suitably greater than 20%, or greater than 30%, or greater than 40%, or greater than 50%, up to 80%.

"Closed surface" refers to a liquid barrier surface having no, or substantially no, open cells or open area. Specifically, a closed surface should have less than about 5% open area, suitably less than about 3%, or less than about 1%, or no open area.

"Hybrid foam layer" refers to a foam layer having an open surface, an opposing closed surface, and an overall open-cell content at least 50%, measured using ASTM D2856.

"Integrated hybrid foam layer" refers to a hybrid foam layer which is formed as a single layer, from a single extrusion die, and therefore has a substantially uniform polymer composition.

DETAILED DESCRIPTION OF THE INVENTION

Referring to FIG. 1, a hybrid absorbent thermoplastic foam 10 includes an integrated hybrid thermoplastic foam layer 12 having an open surface 14, a closed surface 16 and a body 18 having a thickness "T" defined by the distance between the open and closed surfaces. The open surface 14 has an open area greater than 10%, suitably greater than 20%, or greater than 30%, or greater than 40%, or greater than 50%, measured using the Open Area Test described below. The open area is defined by small openings or apertures 62 which extend into an open-cell portion 22 of the body 18. Alternatively, the open-cell foam portion 22 may extend to the surface 14 to provide the open area. The body 18 has an overall open-cell content of about 50% or greater, or about 60% or greater, or about 70% or greater or about 80% or greater, measured using ASTM D2856. The closed surface 16 provides a barrier to the passage of aqueous liquids, and has an open area content of less than 5%, or less than 3%, or less than 1%, or zero.

The body 18 includes an open-celled portion 22 extending inward from the open surface 14 and a closed portion 24 extending inward from the closed surface 16. The open-celled portion 22 may extend to the open surface 14, or may begin a short distance inward from the open surface 14. The open-celled portion 22 and closed portion 24 interface at a boundary 23. The boundary 23 is defined by the position where all cells immediately adjacent to the boundary 23 are at least 50% open only on one side of the boundary 23, and not on both sides. The open-celled portion 22 should constitute at least 50% of the thickness T, suitably at least 70% of the thickness T, or at least 90% of the thickness T, or at least 95% of the thickness T. In other words, the closed portion 24 which defines the closed surface 16 should constitute only a minor portion of the thickness T of body 18.

FIG. 2 illustrates a hybrid absorbent thermoplastic foam 20, in the form of a laminate which includes two of the integrated hybrid thermoplastic foam layers 12. In the embodiment shown, the integrated hybrid foam layers 12 are bonded together only in edge regions 26, leaving a pouch or open space 28 defined by the opposing closed surfaces 16 and the bonded edge regions 26. The hybrid absorbent foam laminate 20 thus has two outer open surfaces 14 and two inner closed surfaces 16. A less expensive laminate, useful as a mitt or glove, may include an integrated hybrid foam layer only on one side and a thermoplastic film or nonwoven web on the other side.

The hybrid absorbent foam laminate 20 can be used to form a wide variety of personal care absorbent articles, medical absorbent articles, and industrial absorbent articles where liquid absorbency and/or liquid delivery are desired in an outer region or surface and liquid barrier is desired in an inner region or surface. Exemplary absorbent articles include without limitation a mitt 30 in FIG. 3(a), including a thumb region 32, a four-finger mitt region 34 and a cuff 36; the two-finger glove 40 in FIG. 3(b), including a thumb region 42, two finger-holding regions 44 and 46, and a cuff region 48; and the four-finger glove 50 shown in FIG. 3(c), including a thumb region 52, four finger-holding regions 53, 54, 55, and 56, and a cuff region 58. The mitt 30 may be used for delivering a liquid such as a cleaning fluid, lotion, antiseptic, or the like.

The hybrid absorbent foam laminate 20 is shown in a simple, relatively inexpensive configuration. Additional layers may be added to provide increased comfort or structural integrity. For instance, woven or nonwoven layers (not shown), such as spunbond, scrim, or meltblown webs, can be provided inward of the closed surfaces 16 to provide the resulting absorbent article with a soft, fabric-like feel on the side which contacts the wearer.

The bonded edges 26 of the hybrid absorbent foam laminate 20 may be formed using any suitable bonding technique. Suitable bonding techniques include thermal bonding, ultrasonic bonding, adhesive bonding, stitch-bonding or the like, and combinations thereof. The optimal bonding technique and conditions will depend on the particular absorbent article being manufactured, and the bond strength requirements.

Figure 4:
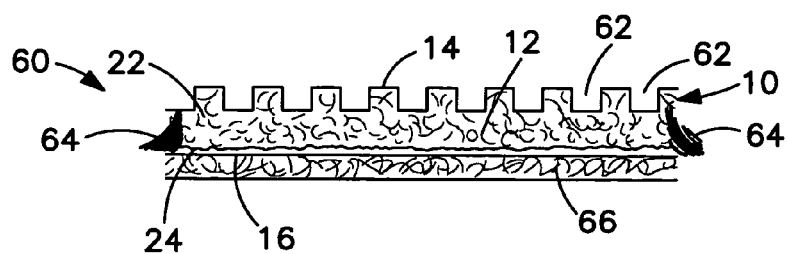
FIG. 4 is a sectional view of a wipe that can be formed from the hybrid absorbent foam, alone or in combination with other layers.

FIG. 4 illustrates an absorbent laminate 60 which can be employed as a wipe, and/or a cleaning fluid dispenser, and can be tailored to a variety of personal care, medical, and industrial absorbent articles and applications. Absorbent laminate 60 includes an integrated hybrid thermoplastic foam layer 12 in which the plurality of apertures 62 (or, alternatively, debossments) extend inward from the open surface 14 and at least partially through the open-cell portion 22, but do not extend into or through the closed portion 24 or to the closed surface 16. The apertures 62 are useful for receiving and distributing a deliverable fluid such as a disinfectant, cleaning fluid, or the like, in the open-cell portion 22, and for later controlled release and dispensing the deliverable fluid, typically by squeezing the absorbent article 60. The absorbent laminate 60 has many fluid delivery properties of a conventional sponge including cellulosic sponges, and thermoset (e.g., polyurethane) sponges. The integrated hybrid absorbent foam layer 12 has densified, compressed end regions 64 which seal and act as a barrier to the fluid in the absorbent laminate 60 by preventing lateral spillage. The densified, compressed end regions 64 can be formed using thermal compression bonding techniques.

In effect, the deliverable fluid is contained within the integrated hybrid foam layer 12 on three sides, bounded by the closed portion 24 and the compressed sealed end regions 64. A plastic or coated paper liner film (not shown) can be positioned adjacent to the open surface 14 to further contain the fluid during packaging and storage of the absorbent laminate 60.

The illustrated absorbent laminate 60 can also include a structural layer 66 laminated to the closed surface 16. The structural layer 66 can be a nonwoven web (e.g. a film, scrim, spunbond or meltblown web, or another material), or a much stiffer and stronger material, depending on the application. If the absorbent laminate 60 is employed as a personal care wipe or mitt, or medical wipe or mitt, for instance, the structural layer 66 will likely be contacted with a user's hand, and should be soft and flexible. If the absorbent laminate 60 is employed as an industrial wipe, the structural layer 60 should be stiff and strong.

Figure 5A:
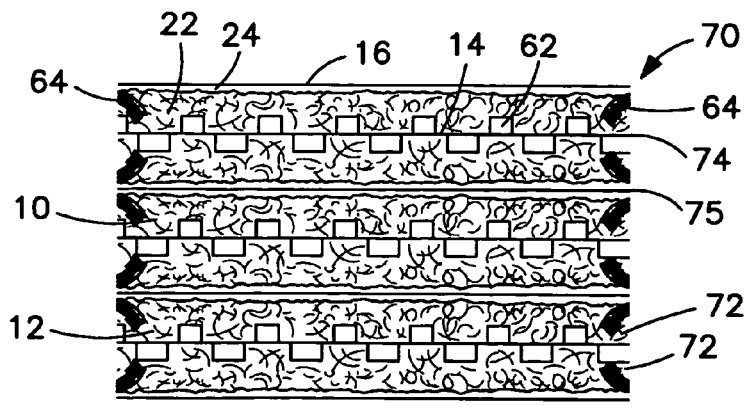
FIG. 5A is a sectional view of a stack including a plurality of wipes temporarily joined at their edges.

FIG. 5A illustrates a stack 70 of absorbent laminates 72, with each of the absorbent laminates 72 being similar to absorbent laminate 60 (FIG. 4) except for the absence of an additional structural layer 66. The absorbent laminates 72 are stacked in pairs, such that the open surface 14 of each integrated hybrid foam layer 12 faces the open surface 14 of an adjacent integrated hybrid foam layer 12. This stacking arrangement helps retain the deliverable fluid within the open-celled portion 22 of each integrated hybrid foam layer 12 during packaging and storage of the absorbent laminates 72. Prior to their use as wipes or mitts, the absorbent laminates 72 may be bonded together at their edges with peelable bonds 74 and 75, which are easily overcome by pulling the absorbent laminates 72 apart.

Figure 5B:
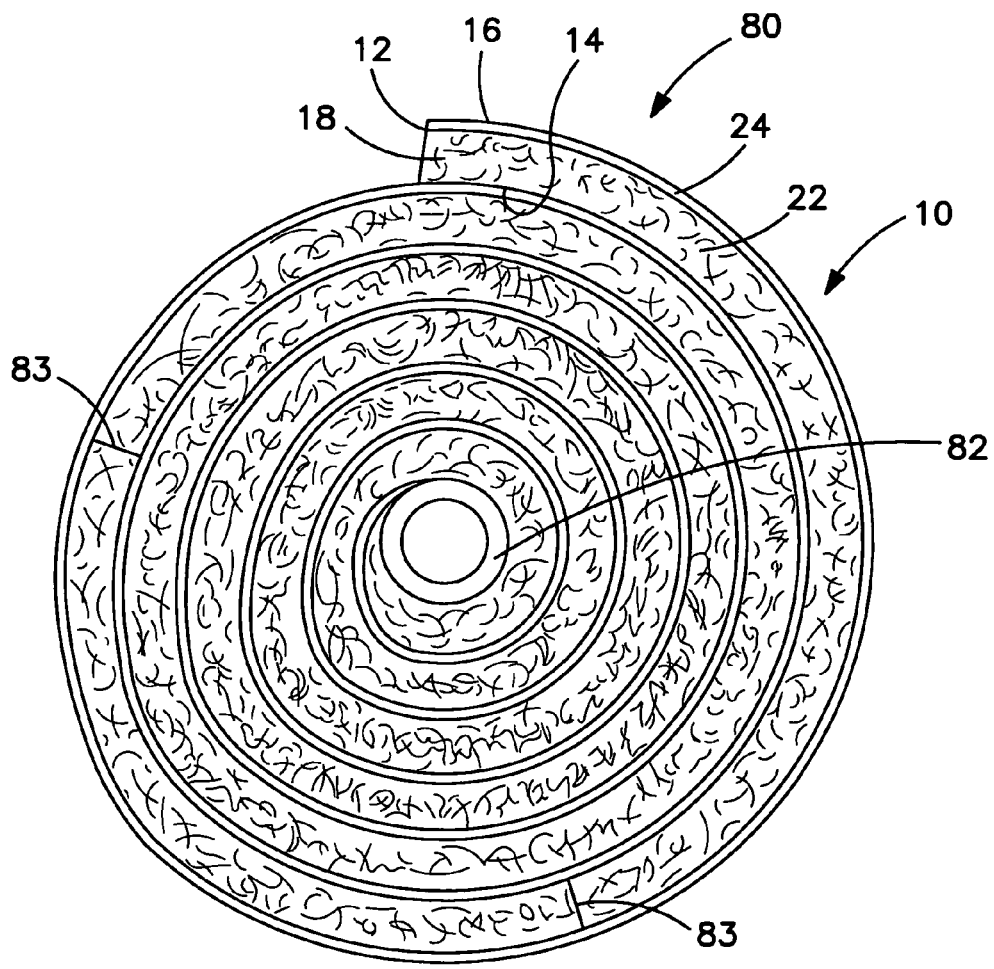
FIG. 5B is an end view of a rolled product, such as a roll of wipes or towels, made using the integrated hybrid foam layer of FIG. 1.

FIG. 5B illustrates a rolled product 80, such as a roll of wipes or towels, formed of the hybrid absorbent thermoplastic foam 10 of FIG. 1 wound onto a core 82. The hybrid absorbent foam 10 can be wound like paper towels and can include tear perforations, but differs from paper towels in that the hybrid absorbent foam 10 is resilient so that absorbed liquid can be squeezed out and the foam 10 can be reused. The hybrid absorbent foam 10 also dries quickly, compared to cellulose absorbents, after being squeezed.

The roll 80 of hybrid absorbent foam 10 can be divided into individual wipes or towels joined along tearable perforated seams 83 similar to the seams joining paper towels. The wipes or towels can be used in cleaning and wiping applications such as dishes, countertops, floors, stovetops, sinks, windows, automobile exteriors and interiors, and the like. The hybrid foam sheets can also be used as an absorbent liner for meat cutting boards, or for drying applications (such as drying an automobile exterior or pet). The roll 80 of hybrid absorbent foam 10 can also be pre-saturated with a deliverable fluid for various cleaning applications. The closed surface 16 faces the user, and is beneficial in protecting the user from skin contact with the deliverable fluid. In another embodiment, the absorbent laminate 60 of FIG. 4 can also be combined with a core 82 and wound into a roll. When the roll 80 is pre-saturated with a deliverable fluid, it may be desirable to contain the roll 80 in a closed container to prevent evaporation of the fluid.

The integrated hybrid thermoplastic foam layer 12 can be produced from various thermoplastic foaming compositions, including the compositions described below. Continuous plastic extrusion processes can initially be utilized to produce an integrated open-celled foam layer having barrier surfaces on both sides, followed by post-treatment process(es) tailored to remove or open up only one of the barrier surfaces, but not the other. Tandem-type extruders are suitably used for making the integrated foam layer because of the need for precise control of extrusion temperatures to produce open-cell foam. The first extruder typically contains several zones including: feed and conveying, compression, melting, metering, and mixing zones and if one extruder is being used, a cooling zone prior to polymer melt discharge, foaming, shaping, and post-treatment. The first extruder is typically hopper-loaded with resin and additives using dry/blend/metering equipment and/or having the additive(s) incorporated into the pelletized polymer concentrate such as in a masterbatch. The resins, additives, and/or masterbatch are then heated in the extruder to form a plasticized or melt polymer system, often with zoned temperature control using extruder cooling/heating systems. Physical blowing agents are typically added after the melt temperature has been heated to a temperature at or above its glass transition temperature or melting temperature to form a foamable melt. The inlet for a physical blowing agent is typically between the metering and mixing zones. The blowing agent can be added at or above saturation levels to meet desired low density targets. The blowing agent is mixed thoroughly with the melted polymer at a sufficiently elevated pressure to prevent melt expansion. With a nucleating agent and blowing agent blended in the polymer melt, the foamable melt is typically cooled to a lower temperature to control the desired foam cell structure. With tandem extruders, the cooling is done in a second extruder which is connected downstream of the first extruder through a heated cross-over supply pipe. In single extruders, including twin screw extruders, cooling is typically done upstream of the discharge orifice. Often cooling/heating systems with process temperature control loops are incorporated to tightly control foam bubble nucleation/growth within the melt. The optimum cooling temperature is typically at or slightly above the glass transition temperature or melting point of the melt.

Figure 6:
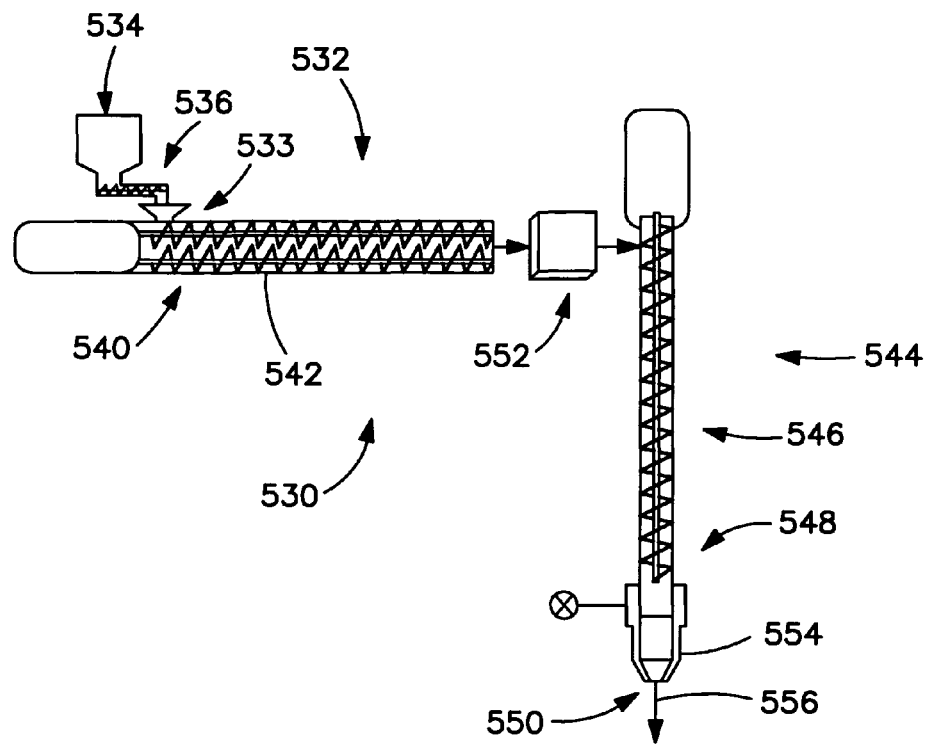
FIG. 6 schematically illustrates a tandem extrusion process useful to make the hybrid absorbent foam.

In one embodiment, a tandem extruder, such as illustrated in FIG. 6, can be utilized. This type of extruder arrangement 530 may be considered particularly suitable in some aspects because it has the ability to provide precise control of extrusion temperatures to produce open-cell foam. With tandem extruders 530, the first extruder section 532 typically contains several zones including a feed zone 534, a conveying zone 536, a compression zone 538, a melting zone 540, and a metering and mixing zone 542. The second extruder section 544 often contains a cooling zone 546 and a shaping zone 548 prior to the discharge 550. The first extruder 532 is typically hopper-loaded with the base resin(s) as well as any other desired additives, including thermoplastic elastomers, plasticizing agents, surfactants and/or fibers, for example. Techniques known in the art for accomplishing this include using dry blend/metering equipment and/or having the components incorporated into a pelletized polymer concentrate such as in a masterbatch. The components of the foam formula are then heated in the extruder 532 to form a plasticized or melt polymer.

The foamable melt is then typically cooled to a lower temperature to control the desired foam cell structure. In the case of tandem extruders 530, the cooling is typically accomplished in the second extruder 544 which is connected downstream of the first extruder 532 through a heated cross-over supply pipe 552. In the case of single extruders (not shown), cooling is typically accomplished upstream of the discharge orifice. Often cooling/heating systems with process temperature control loops are incorporated to tightly control foam bubble nucleation/growth within the gas-laden melt. The optimum cooling temperature for foam formation is typically at or slightly above the glass transition temperature or melting point of the melt.

The melt is then extruded through a die 554 to a lower pressure (typically atmospheric or a vacuum) and lower temperature (typically ambient) environment to cause thermodynamic instability and foaming that cools and crystallizes the polymer composition to form a stabilized foam 556 that solidifies to form an integrated foam layer. Circular, annular or slit dies, including curtain dies, and the like can be used, often with a mandrel, to shape and draw the foam to the desired gauge, shape, and orientation with foam expansion and cooling. When the polymer composition is extruded as a thin foam layer, dual sluice dies can be used to form a suitable closed surface on one side, having fluid barrier properties.

Various equipment configurations using such extrusion means can be used to manufacture the foam composite of the present invention. In addition, various specialized equipment can be employed upstream of specially designed dies to enhance mixing, cooling, cellular structure, metering, and foaming. Such equipment includes static mixers, gear pumps, and various extruder screw designs, for example. Stretching equipment, including roller nips, tenters, and belts, may also be used immediately downstream of the discharge to elongate cellular shape to enhance absorbency, for example. Microwave irradiation for cross-linking, foaming activation, and mechanical means can also be used to enhance foam properties. Foam contouring, shaping (e.g., use of a wire mesh pattern), and the like, using thermoforming, and other such thermal processes, including thermal bonding and creping, can be used to control shaping, flexibility, softness, aesthetics, and absorbent swelling.

Both physical and chemical blowing agents, including both inorganic and organic physical blowing agents, are used to create foaming. Suitable inorganic physical blowing agents include water, nitrogen, carbon dioxide, air, argon, and helium. Organic blowing agents include hydrocarbons such as methane, ethane, propane, butanes, pentanes, hexanes, and the like. Aliphatic alcohols and halogenated hydrocarbons, including FREON® and HFC-134A, can also be used though in the latter, their use is generally avoided for environmental reasons. Endothermic and exothermic chemical blowing agents which are typically added at the extruder hopper include: azodicarbonamide, paratoluene sulfonyl hydrazide, azodiisobutyro-nitrile, benzene sulfonyl hydrazide, P-toluene sulfonyl hydrazide, barium azodicarboxylate, sodium bicarbonate, sodium carbonate, ammonium carbonate, citric acid, toluene sulfonyl semicarbazide, dinitroso-pentamethylene-tetramine, phenyltetrazole sodium borohydride, and the like. Mixtures and combinations of various physical and chemical blowing agents can be used and often are used to control cell structure. Blowing agent activators can be added to lower the decomposition temperature/profile of such chemical blowing agents. Such activators include metals in the form of salts, oxides, or organometallic complexes.

Open-cell formation can be regulated by elevated processing pressures and/or temperatures and use of nucleating agents and chemical blowing agents which can control both cell density and cell structure. Various base resins are sometimes used to broaden the foaming temperature to make open-cell foam. Open-cell level can be facilitated by adding small amounts of various immiscible polymers to the foam polymer formula such as adding polyethylene or ethylene/vinyl acetate copolymer to polystyrenic-based foam systems to create interphase domains that cause cell wall rupture. By regulating the polymer system components and crystallization initiating temperature, open-cell content and microporous cell membrane uniformity can be controlled. Ethylene-styrene interpolymers can be added to alkenyl aromatic polymers to control open-cell quality and improve surface quality and processability. Small amounts of polystyrene-based polymers are sometimes added to polyolefin-based foams to increase open-cell content. Small amounts of polyolefins can be added to improve fluid barrier properties of the closed surface of polystyrene-based foams.

Additives, such as nucleating agents, can also be employed to obtain desired fine open-cell structure. The amount of nucleating agent will vary according to the cell structure desired, foaming temperature, pressure, polymer composition, and type of nucleating agent utilized. Typically with increasing nucleating agent, cell density and open-cell content increase. Nucleating agents include calcium carbonate, blends of citric acid and sodium bicarbonate, coated citric acid/sodium bicarbonate particles, nanoclays, silica, barium stearate, diatomaceous earth, titanium dioxide, talc, pulverized wood, clay, and calcium stearate. Stearic acid, salicylic acid, fatty acids, and metal oxides can also be used as foaming aids. Other thermoplastic polymers can also be used for such purposes. These are typically dry-blended or added with the polymer concentrate.

Various additives such as lubricants, acid scavengers, stabilizers, colorants, adhesive promoters, fillers, smart-chemicals, foam regulators, various UV/infrared radiation stabilizing agents, antioxidants, flame retardants, smoke suppressants, anti-shrinking agents, thermal stabilizers, rubbers (including thermosets), anti-statics, permeability modifiers, and other processing and extrusion aids including mold release agents, and anti-blocking agents, and the like can also be added to the foam polymer formula.

The open-celled foam produced by this process typically has thin skins defining barrier surfaces on both sides, followed by a smaller layer of a population of closed cells, followed by open-celled foam between the barrier skins. In the thermoplastic extrusion process used to make the foam, the outside surfaces of the foam form impervious film-like skins. The skin surfaces are formed with rapid cooling of the outside surfaces upon exiting the extrusion die and help contain entrapped gas within the polymer melt long enough for gas diffusion to sufficiently allow foam expansion and polymer structural solidification. With the rapid cooling of the polymer melt into a foam structure, an impervious closed-cell foam structure is typically formed directly beneath the skin surface. Beneath the closed cellular structure in the middle portion of the foam laminate is an absorbent open-cell structure. The outside film skin surfaces and closed-cell structures are dense and form an "I-beam-like" structure that increases sheet stiffness. These structures also form a fluid and/or vapor barrier. Fluid and vapor absorbent products must have access to this middle open-cell foam structure. To make the integrated hybrid foam layer of the invention, the skin defining the barrier surface can be removed from only one side, and not the other. This can be accomplished using various post-treatment process techniques. For instance, the barrier surface on only one side may be skinned, sliced off, needle-punched, brushed, scraped, sanded, buffed, scarved, or perforated. Following is a detailed discussion of several post-treatment processes used to remove the barrier surface from one side of the foam.

A) Pin Microaperturing

To aperture the foam on one side, driven nip rolls wrapped with Redman flexible wire cloths from Redman Card Clothing Co., Inc. of Andover, Mass., USA, can be employed. For a foam which is 2-4 mm thick, the flexible wire cloths may have pins arranged normal to the nip rolls and the foam sheet and may have diameters of about 0.010-0.18 in (0.254-4.57 mm), pin densities of about 192-312 pins/in$^2$ (30-48 pins/cm$^2$), and pin heights of about 1.6-2.4 mm. It has been found that pin density, pin diameter, and the number of nip treatment passes have quantifiable impacts on foam fluid intake.

The short pin heights of the flexible wire cloths are useful to mechanically aperture the foam on one side, thereby effectively permeating the barrier skin and impermeable closed cells on only one side. The pins are shorter than the thickness of the foam, so as to not completely penetrate through the foam sheet to the other side. Also, the smaller pin diameters referenced above provide apertures which are small enough so as not to Z-directionally crimp the foam (given that crimping impairs fluid access). Suitable wire cloths include Redman PRKC-4 and PRKC-11 having pin heights of 2.4 mm and 1.6 mm, pin densities of 192 pins/in$^2$ (30 pins/cm$^2$.) and 192 pins/in$^2$ (30 pins/cm$^2$), and pin diameters of 0.010 in (0.254 mm) and 0.014 in (0.356 mm), respectively. Seven passes with these microaperturing wire roll nips were found to provide the foam with enhanced tactile aesthetics and absorbent functionality including fluid intake and saturated capacity. The optimal number of passes may vary depending on the application.

The enhanced flexibility imparted with microaperturing not only improves absorbency and softness but improves surface texturing (described in Section C below). Microaperturing increases sheet flexibility which allows better sheet contact with the moving surface texturing raising fillets or pins and disrupts the foam film's outer skin film-like surface to make it less smooth. The microaperturing also instills a raised surface topography so that surface texture raising/sueding pins can more readily "grab" and texture the foam to induce cloth-like and suede rather than plastic-like visual and tactile aesthetics.

Microaperturing coupled with surface texturing can serve at least five functions: 1) improved tactile and visual aesthetics, 2) increased softness and flexibility, 3) enhanced absorbency properties such as capacity, wicking, and intake, 4) reduced piling and lint, and 5) minimized loss in sheet strength without unacceptable basis weight loss. Microapertured foams with sufficient access to the absorbent open-cells can be used for personal care, wipes, matts, carrier media, filters, and other absorbents. In addition, tortuous air flow permeability can be increased 1000× with microaperturing and thereby can allow the foam to be engineered for construction barrier/thermal and sound insulation, and controlled fluid release applications.

Use of flexible wire cloths for microaperturing is significantly less expensive, and yields better properties, than conventionally fabricated pin aperturing rolls (machined rolls with pressed pins). Besides the cost advantages, such wire cloths can also readily be patterned for different X-Y-Z penetration patterns. Because of the low equipment cost, high hole density treatments can be employed by utilizing several in-line microaperturing rolls. Because honeycombed, micro-size, non-through hole aperturing rather than through-hole or slit aperturing is being utilized, the sheet's integrity remains high and sheet tear propagation is minimized.

Microaperturing can also be enhanced by heating the pins. With heated pin microapertured thermoplastic foam, it was seen in microphotographs that hole size increased from the retraction of the polymer film that formed the fine thin cellular walls when the heated pins penetrated into the foam structure. The heated pins were of sufficient length to penetrate into the internal open-cell structure. This allowed for a larger effective hole diameter for better fluid intake without damaging Z-directional open-cell cavities so fluid was readily absorbed into the foam's internal structure. By comparing cold (room temperature) vs. heated (65° C.) pin microaperturing, a smaller heated pin microaperturing density is needed to obtain improved fluid intake using the Single Drop Test (below). Initial fluid intake time of 3-5 seconds could be obtained with one heated pin microaperturing roll nip pass. With cold pin microaperturing, seven roll nip passes were used to produce a 10 second intake time. Wire cloth dimensions, roll nip pressures, and number of microaperturing roll passes were evaluated and found to affect absorbent rates. In addition, if the foam's surface had previously been surface textured and then vacuumed to remove excess lint and debris, reduced Tinting and piling occurred after heated pin microaperturing. With heat, loosely bound surface protuberances and piles were more securely thermally bonded to the base foam surface. Thermally treating the surface textured foam with a heat gun or oven also reduced linting. Abrasion resistance improved.

To reduce equipment fabrication cost, one microaperturing roll design option is to use an internally heated microaperturing roll and a heat-resistant flexible wire cloth. The heated roll would readily transfer heat to the metal aperturing pins. With the pins being in contact with the heated roll surface, heat conductance would readily occur with a heat-resistant silicon-impregnated wire cloth being less conductive and acting as an insulator. Such heat-resistant wire cloth can be obtained from Redman Card Clothing Co., Inc.

Figure 16A:
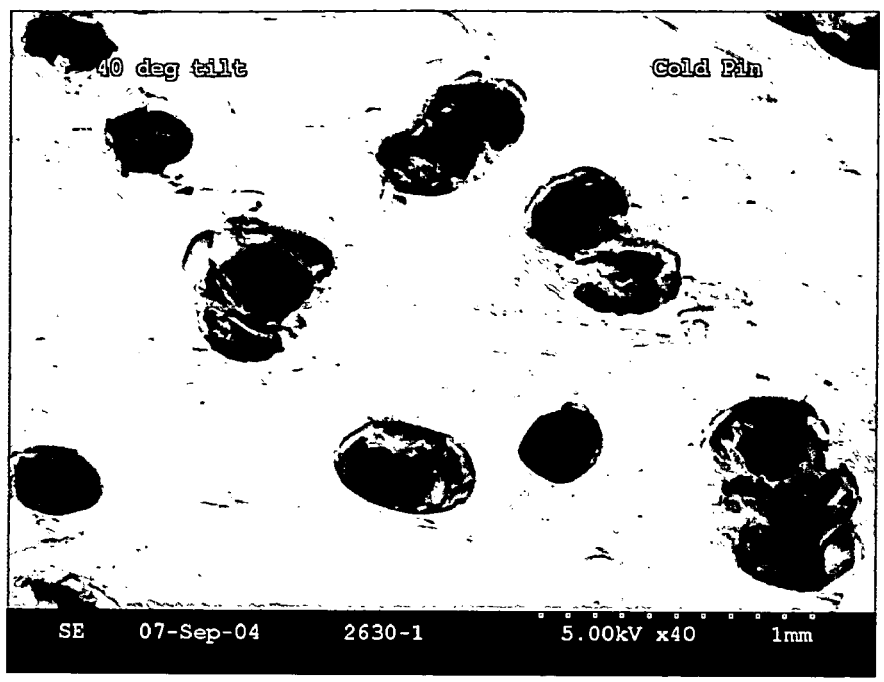
FIGS. 16A and 16B are SEM photographs illustrating the open surface of a representative hybrid absorbent foam of the invention, post-treated using cold pin microaperturing.
Figure 16B:
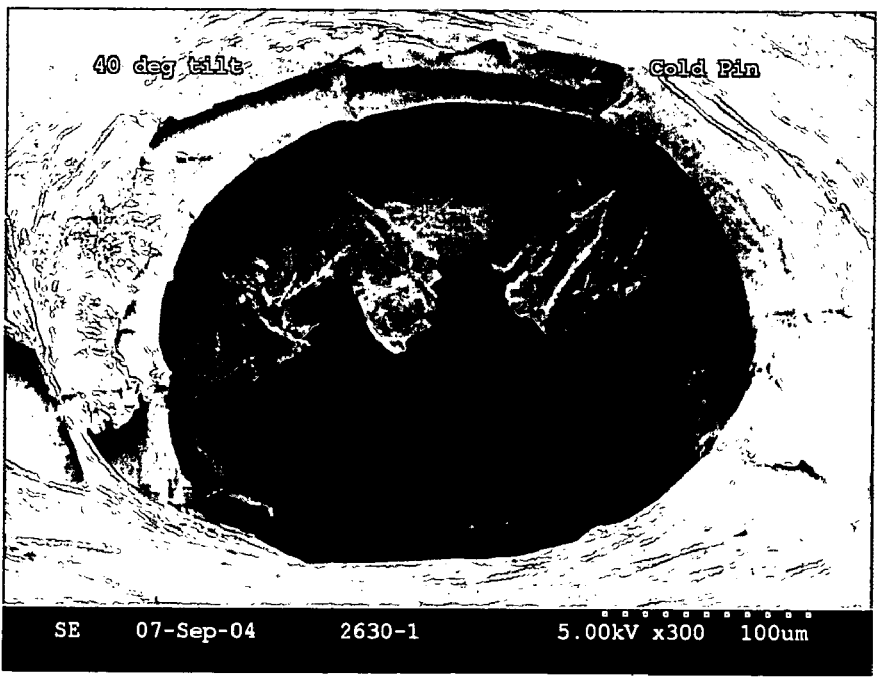
Figure 17A:
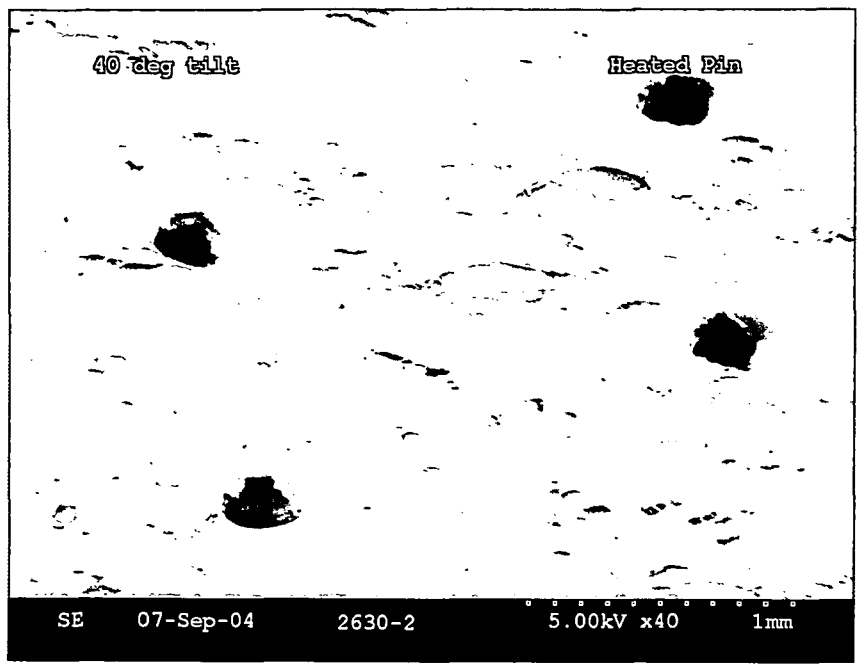
FIGS. 17A and 17B are SEM photographs illustrating the open surface of a representative hybrid absorbent foam of the invention, post-treated using heated pin microaperturing.
Figure 17B:
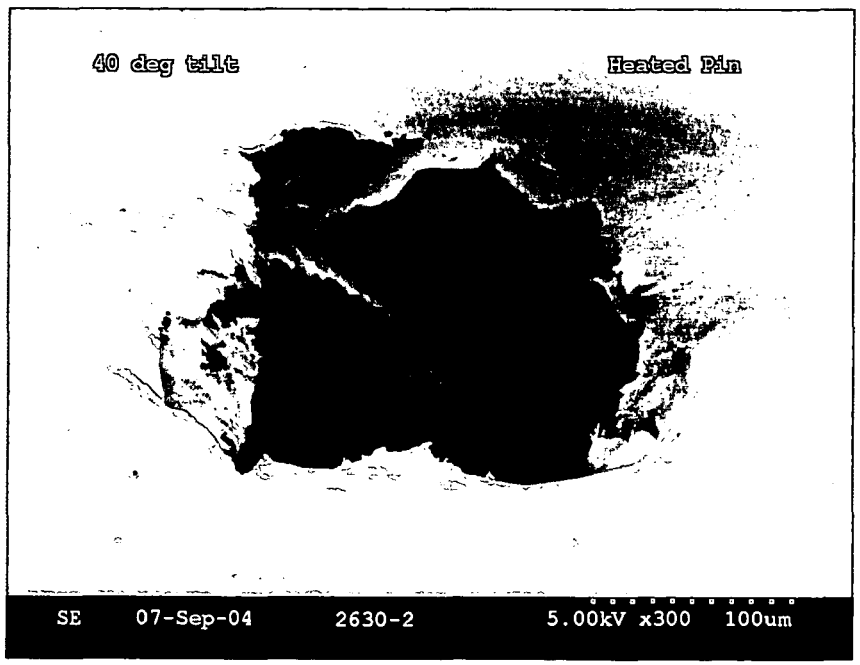

FIGS. 16A and 16B are SEM images of the open surface of a representative integrated hybrid foam layer of the invention, post-treated using cold pin microaperturing. FIGS. 17A and 17B are SEM images of the open surface of the representative integrated hybrid foam layer, post-treated using heated pin microaperturing. Either technique produces a suitable hybrid absorbent foam.

B) Slitting

Both micro and macro-slitting of the foam can be employed to slit the foam on one side, thus leaving one of the barrier skins intact. Using various ultrasonic anvils, different slitting patterns were evaluated including a preferred "crowfoot" pattern. To slit only one skin, partially Z-directionally slit apertured arrangements were produced. With machine adjustment, slits could be produced that did not crimp the internal hole structure. Various foam basis weights and densities could be slit. In addition, spunbond could be bonded to the foam using ultrasonic anvils.

Utilizing fine columnar hydraulic jets (spunlace technology), micro-slits have been imparted into the foam to enhance absorbency, softness, and flexibility. This technology has its drawbacks in jet non-uniformity and web sensitivity to high pressure needling jets causing excessive micro-slitting that often results in diminished integrity, and increased tear propagation and rupturing of the closed barrier surface. There is also the need to dry the foam of water after hydraulic jet treatment for dry sheet product applications.

By retrofitting one or more surface texturing raising or sueding rotating rolls covered with an engineered flexible wire cloth having longer protruding pins than the base height, pins can be strategically spaced and located circumferentially around the roll to micro-slit foam. The rotating roll is speed controlled so that with a given web speed, the longer protruding pins intermittently micro-slit a taut-stretched foam sheet by "scratching out" a narrow furrow within the surface of the foam skin sufficiently deep enough to penetrate the open-cell absorbent structure. This instills slitting in the machine direction of the foam and the micro-slitting depth is adjustable. Such a design can be installed in surface texture raising/sueding equipment, and the rotating roll height can be adjusted for controlled foam sheet micro-slitting. The sheet can be stretched taut across a rotating raising or sueding drum or moving flat bed and fixed to insure the desired slitting depth.

C) Surface Texturing

Mechanical brushing (scarfing) of the foam's skin can be employed to remove one of the barrier skins to diminish the plastic-like aesthetics and penetrate the closed-cells to allow fluid access to the open-cell structure. Steel wire brushes can surface texture the foam but it was determined that more sophisticated brush rolls would be required to minimize excess removal of material and loss of web strength. Atlanta Brush, Inc. of Atlanta, Ga., U.S.A. can supply such trimmed brushes. However, even these brushes can be too coarse for foam. With this, textile raising and sueding machinery using fine flexible surface texturing wire cloths having specifically designed raising or teasing fillets was coupled with microaperturing. By optimizing machine conditions, acceptable foam samples were produced having good integrity, absorbency, and visual/tactile aesthetics. Using Redman raising wires and Saspe's RapidRaise®/Velura and Durasuede®/VersaTouch textile machinery, aesthetically appealing surface textured foam can be produced. This equipment can be obtained from Saspe S.r.l. of Schio, Italy. The RapidRaise® process requires relatively minimum required web tension versus sueding where web tension is much higher to obtain the necessary working action.

Textile surface texturing equipment has a high processing efficiency making it a plausible candidate for in-line foam extrusion. Fine tuning of the machine setup is necessary to obtain desired properties. Because of the foam's formulation producing a sheet having high web strength, elasticity, flexibility, resiliency, and toughness, the sheet is able to withstand the raising fillets' dynamic and impulsive loadings The foam skin acts like an "I-Beam." With partial removal of the skin surface from one or both sides and microaperturing, the softness and flexibility of the web dramatically improves. With one-side treatment, fluid barrier properties can be maintained on the closed surface. If it is desired to surface texture both sides for tactile aesthetics, optimum control of surface texturing is needed to avoid penetrating the barrier skin. If desired, the barrier skin can be made thicker using dual sluice dies and specially designed single opening dies. With a fibrillated or suede-like outer-layer surface, visual and tactile aesthetics are much more cloth-like. By combining raising and/or sueding and microaperturing, foams have been produced having:

Basis Weight losses typically of <10%
Grab MD Tensiles of 10000 grams
MD Trap Tears of >900 grams
Grab CD Tensiles of 7000 grams
CD Trap Tears of >350 grams
First intake fluid intake flux rates ~5 ml/sec.
Fluid Retention Capacities of >7 g/g
Vertical Wicking of >8.0 cm By removing ~10% or more of the basis weight from the surface of non-microapertured foam, high fluid intake flux intake rates could be gained; however, the high basis weight loss is not desirable. Various process and equipment designs include fixing the web to the rotating raising drum and rolls, fixing the foam to a rotating drum or moving flat-bed, and rotating the surface texturing rolls to finely remove or tease the foam skin surface.

Figure 18A:
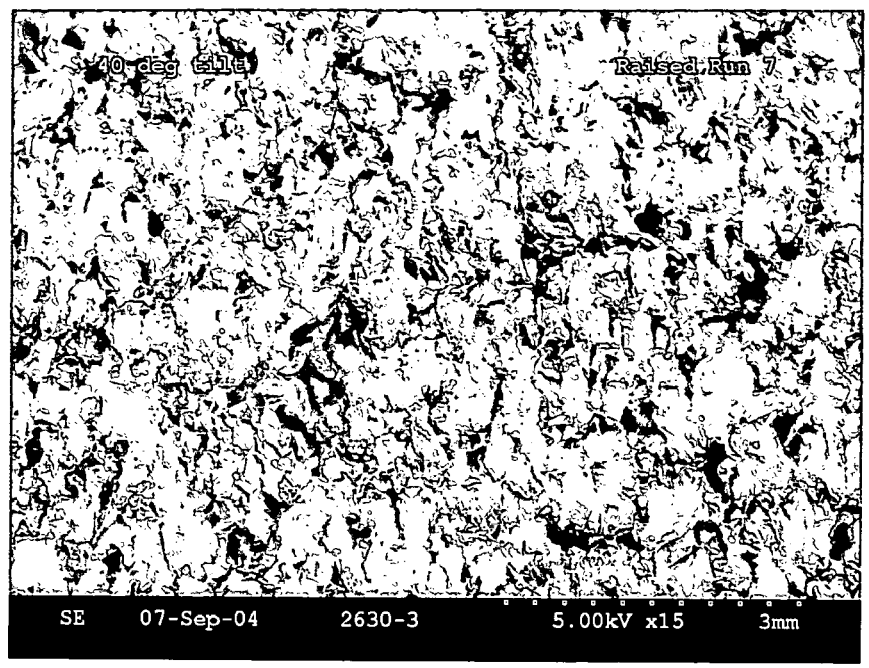
FIGS. 18A and 18B are SEM photographs illustrating the open surface of a representative hybrid absorbent foam, post-treated using surface texturing.
Figure 18B:
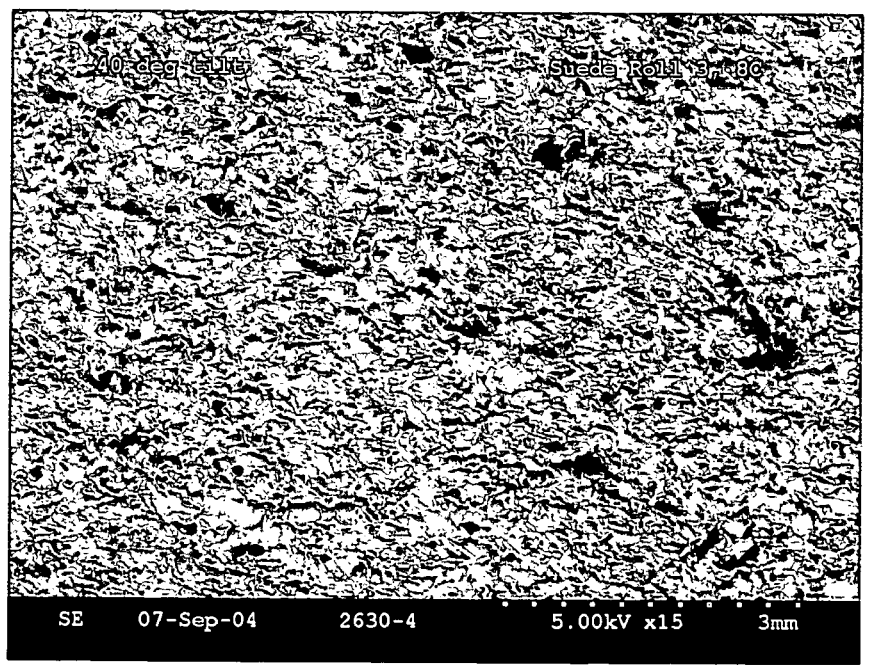

FIG. 18A is a scanning electron microscopy ("SEM") photograph of an open surface of a representative integrated hybrid foam layer, post-treated by raising. FIG. 18B is a SEM photograph of an open surface of a representative integrated hybrid foam layer, post-treated using a combination of sueding and micro-aperturing.

D) Hydraulic Needling

Hydraulic needling is one approach to remove, puncture, or micro-slit one skin of the foam. The pressure in the water jets, the water columnar diameter, the jet density, the speed at which the web passes through the jets, the foraminous sheet support backing, the vacuum dewatering levels, and the number of passes (or number of banks of jets) determine the level to which the skin layer is removed. Several thermoplastic foams have been treated in this manner to enhance properties. In addition to skin layer removal, an increase in open-cell content and liquid accessible pore space has been demonstrated.

Several polystyrene-based extruded foams of the invention (Foams D1-D4 below) made on a pilot line were hydraulically needled at different pressures (4000-7000 KPa) using a hydraulic needling tablewasher. Scanning Electron Microscopy of the needled foams show that the skin layer was punctured, allowing access to the open cells below. The data in Table D1 (below) shows that hydraulic needling at the stated pressures improves the absorption capacity, vertical wicking height, and open-cell content of the foam.

about 500 to about 1000 pounds per square inch gage (psig) (3447 to 6895 KPa), such as about 600 to about 800 psig (4137 to 5516 KPa). In general, the integrated foam layers may be hydraulically needled on one side using one to four manifolds. Greater energy, including intermittently impulsed needling energy, may be needed if the hydraulic needling, in addition to perforating one of the skins, is used to form apertures 62 (FIG. 4), or when high line speeds are employed.

Water jet treatment equipment and other hydraulic needling equipment and processes which may be adapted can be found, for example, in U.S. Pat. No. 3,485,706 to Evans, and in an article by Honeycomb Systems, Inc. entitled "Rotary Hydraulic Entanglement of Nonwovens," reprinted from INSIGHT 86 INTERNATIONAL ADVANCED FORMING/BONDING CONFERENCE, both of which are incorporated herein by reference in a manner consistent herewith. In some aspects, the invention may be practiced using a manifold containing an orifice strip having 0.007 inch (0.18 mm) diameter orifices, 30 orifices per inch (12 orifices per cm), and one row of orifices such as that produced by Metso Paper USA, Inc., a business having offices located in Biddeford, Me.,

TABLE D1

| | Foam D1 | | | Foam D2 | | | Foam D3 | | | Foam D4 | | |
| --- | --- | --- | --- | --- | --- | --- | --- | --- | --- | --- | --- | --- |
| | Control | 4137 Kpa | 5556 Kpa | Control | 5556 Kpa | 6945 Kpa | Control | 4827 Kpa | 5556 Kpa | Control | 5556 Kpa | 6945 Kpa |
| Basis weight (g/m^2) | 249 | 220 | 234 | 313 | 237 | 238 | 227 | 180 | 188 | 252 | 237 | 238 |
| Dry Bulk (mm) | 2.99 | 2.51 | 2.31 | 3.08 | 1.67 | 1.65 | 2.81 | 1.98 | 2.27 | 1.97 | 1.67 | 1.65 |
| Capacity (g/g) | 0.5 | 1.9 | 2.2 | 0.4 | 1.1 | 1.2 | 0.4 | 1.6 | 2.3 | 0.4 | 1.1 | 1.2 |
| Open-cell (%) | 60 | 71 | 80 | 74 | 66 | 63 | 55 | 60 | 70 | 55 | 66 | 63 |
| Vertical wicking (cm) | 4.1 | 7.5 | 8 | 3.1 | 8.2 | 8.2 | 3.2 | 5.1 | 5.3 | 4.2 | 8.2 | 8.2 |

Polystyrene/KRATON® blend foams (Foams D5-D7) were made on a pilot line and hydraulically needled using a hydraulic needling tablewasher at about 5556 KPa. Results from sample characterization are shown in Table D2 (below).

U.S.A. Other manifold configurations and combinations, such as those available from Fleissner GmbH, a business having offices in Egelsbach, Germany, or Rieter Perfojet S.A., a business having offices located in Winterthur, Swit-

TABLE D2

| | Foam D5 | | Foam D6 | | Foam D7 | |
| --- | --- | --- | --- | --- | --- | --- |
| | Control | H-needled | Control | H-needled | Control | H-needled |
| Basis weight (g/m^2) | 150 | 150 | 150 | 150 | 150 | 150 |
| Dry Bulk (mm) | 1.29 | 1.83 | 1.5 | 1.92 | 3.19 | 2.59 |
| Capacity (g/g) | 0.9 | 6.3 | 1.7 | 7.2 | 6.2 | 12.3 |
| Open-cell (%) | 63 | 89 | 82 | 90 | 90 | 94 |
| Vertical wicking (cm) | 10 | 16 | 10 | 15 | 4 | 14 |
| Bending Modulus (MD) (Kpa) | 26290 | 2703 | 28938 | 6516 | 7667 | 2751 |
| Bending Modulus (CD) (Kpa) | 8743 | 1469 | 4675 | 2558 | 4054 | 1089 |

Figure 7:
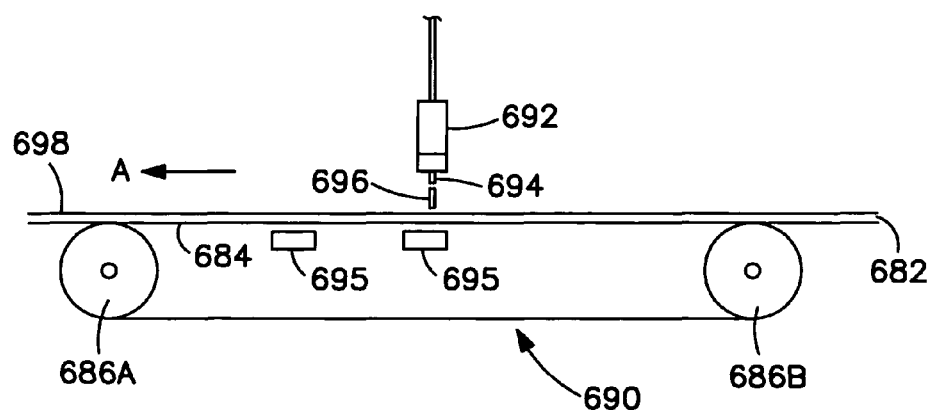
FIG. 7 illustrates a post-treatment process useful to form the open surface to make the hybrid absorbent foam.

FIG. 7 illustrates one suitable hydraulic needling process which can be tailored to perforate only one skin. The hydraulic needling process may be carried out with any appropriate working fluid such as, for example, water. The working fluid is generally evenly distributed by the manifold 692 through a series of individual holes or orifices 694 which may be from about 0.003 to about 0.015 inch (0.076 to 0.391 mm) in diameter and are used to discharge fine columnar jets or needles of fluid. In some aspects, the working fluid passes through the orifices 694 at a pressure generally ranging from zerland, may also be used. For instance, in some aspects a single manifold may be utilized, whereas in other aspects several manifolds may be arranged in succession.

Referring again to FIG. 7, the fine columnar jetted streams 696 of the working fluid impact on the foam layer 682, thereby puncturing only one of the skins formed on the foam layer surfaces during formation and increase the open-cell content of that surface. Vacuum slots in suction box(es) 695 can be located at the jets and downstream of the needling manifold(s) 694 to remove excess water from the hydraulically jet-treated material 698. A foraminous moving wire 690 is generally used to convey and support the foam sheet 682. The hydraulically jet-treated integrated hybrid foam layer 698 can then be dried using means known in the art.

E) Areal Sheet Splitting

Typically, an extruded thermoplastic foam sheet upon being discharged from an extrusion die has z-directional cell shape and size gradients that correspond to how close cells are located proximal to the peripheral skin surfaces. At selected processing conditions, internal cells generally grow to much larger sizes than cells located near the outer surfaces of the sheet. This process can be enhanced where cell walls in the middle of the sheet form a channel for they are nearly non-existent and the cell struts are thin and few in number. Such sheets can be separated along the internal channel where such large open cells form a demarcation.

The method for producing delaminable foam requires a foam extrusion process that produces foam sheets with an internal cell structure that is conducive to delamination or areal splitting. After the sheet is extruded, it is fed through a sheet delaminating station. One option is to have a delaminating station having two vacuum rolls positioned to form a nip opening distance near equal to the foam sheet thickness. The two rolls move at the same synchronized circumferential speeds with two sheet take-off angles aligned downstream of the nip to follow the rolls' radial curvatures to position the sheet's opposite peripheral surfaces to be near normal to the initial sheet path direction. This arrangement allows the sheet to readily split into two separate webs at the sheet's centerline where internal cells are large and few thin struts occur. The sheet vacuum hold down force for each roll must be greater than the sheet travel force to maintain the delaminating or areal splitting action of the foam. With change in sheet direction occurring with the two rolls radial curvatures, the resultant forces cause the sheet to delaminate since both sides of the sheet remain fixed to the rotating vacuum rolls.

Acceptable foam was made on a pilot line using blends of polystyrene, Kraton elastomer, surfactant, and talc, a nucleant. These materials were melted in a first extruder where they were mixed together and combined with blowing agents. The blowing agents were isopentane and carbon dioxide. The gas laden melt was transferred to a second extruder where the melt was cooled before being extruded through an annular die. The melt expanded into foam upon discharge. The foam tube was then stretched and cooled over a mandrel drum and slit into a sheet before being wound into roll form. A single extruder (typically a twin screw extruder) can be used in lieu of the aforementioned tandem extrusion system; however, basic process steps remain essentially the same.

Process conditions are typically optimized for throughput and foam uniformity. Uniformity of cell structure and isotropy of cell shape throughout the sheet are enhanced by ensuring proper mixing of materials and blowing agents and adjusting process conditions that ensure adequate solubility of the blowing agent(s). The method by which a foam sheet is cooled will typically affect cell properties near the peripheral surfaces of a foam sheet. The cells nearest the peripheral surfaces typically collapse and form a skin or film that is non-permeable or nearly non-permeable to fluid. The rate a sheet is pulled from the die opening and across a cooling drum has a major impact on the sheet and the cells making it up. A typical foam manufacturer focuses on cooling the material at a slow enough rate that the blowing agent(s) has (have) time to diffuse through the polymer melt and to form bubbles or cells of sufficient size yet the blowing gas diffusivity is slow enough so the foam cells can gain structural stability. The cooling rate is adjusted by adjusting the environment that the foam can expand into and by controlling the temperature of the surfaces onto which the foam contacts. As the polymer melt cools, gas permeability decreases and the foam sheet tends to retain the blowing agents longer which increases foam cell size. Typical foam manufacturers hold value in having uniform cell size and therefore require careful adjustment and control of cooling to maintain uniform cell size throughout the thickness of the sample. It is possible to adjust the foam process so cellular growth increases in the center of the foam sheet relative to cells near the peripheral surfaces. In this invention, a foam sheet is made that is particularly easy to delaminate or "areal split" along the central internal channel or axis of the sheet and is due to the large cells and few thin struts. "Areal split" means foams that require little force to continuously pull the top surface away from the bottom surface while the two separated webs remain intact and near uniform without unwanted tears.

In summary, process conditions used to make areal splittable foam generally include the following:
1. Upon discharge, the foam surfaces are cooled quickly to reduce the diffusivity rate of the blowing agent(s).
2. The foam is pulled out of the die at a rate at or slightly faster than the velocity of the exiting melt; i.e., causing no stretching and/or cellular elongation.
3. An "excess" of blowing agent(s) is (are) provided to the melt. "Excess" refers to a concentration greater than the typical minimum concentration used to produce the targeted density.

Figure 14:
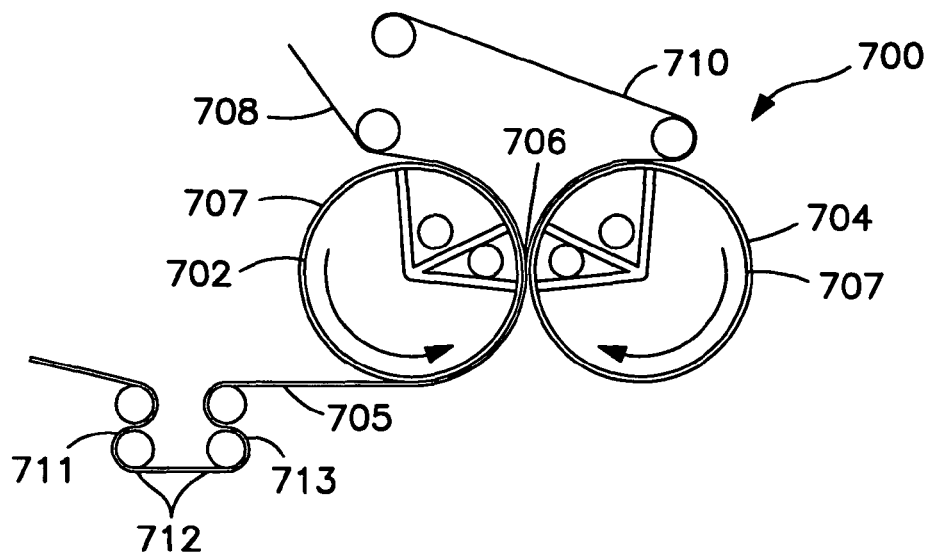
FIGS. 14 and 15 schematically illustrate two areal foam splitting processes used to make integrated hybrid foam layers of the invention.

As shown in FIG. 14, one delaminating process 700 consists of two vacuum rolls 702 and 704 that form a nip 706 and rotate in opposite directions to provide force to pull the top sheet surface 708 away from the bottom surface 710. The foam is held in place against these rolls by the pressure drop across the sheet 705 caused by the vacuum at the surface of the rolls. The vacuum rolls 702 and 704 are designed to prevent substantial deformation of the sheet 705 at the location where the splitting action takes place. This is accomplished with a fine mesh foraminous screen cover 707 on the surface of the rotating vacuum rolls and internal vacuum distribution baffles to evenly distribute the pressure forces and by use of a stretching station 712 to tender and level the sheet 705 before it is fixed to the initial vacuum roll 702. To facilitate the splitting of the sheet, pre-conditioning of the sheet can be performed. Pulling materials through an "S-wrap" 711 as shown will tend to put shear stresses in the sheet 705. These shear forces can break many of the internal thin channel struts that link the top and bottom layers. In addition, rolls 713 positioned immediately upstream of the vacuum rolls can either add heat, or cool the sheet 705 to facilitate efficient and uniform splitting. Cooling the sheet can bring the sheet below its rubber transition facilitating breaking of the struts with less strain. Alternately, heating the sheet can reduce the stress required to break struts.

Figure 15:
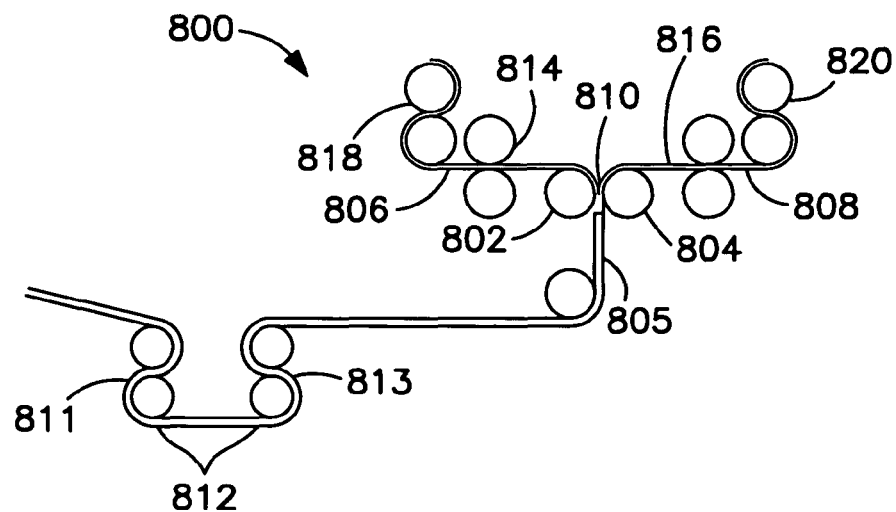

Another delaminating process 800 is shown in FIG. 15 and can be used to split the top surface 806 from the bottom 808. In this apparatus, two small splitting rolls 802 and 804 form a nip 810 and provide surfaces for the sheet 805 to be pulled against. This design provides a method for increasing the rate that sheets are pulled apart. Small splitting roll radii create fast splitting rates. With this device, the distance between the splitting rolls can be controlled to nip the foam 805 so it has a sheet speed equal to the circumferential speeds of the two synchronized rotating rolls 802 and 804. A driven pull roll system including nips 814 and 816 and S-roll nips 818 and 820 can be used to put tension in the sheet that is sufficient to split the foam sheet apart. Again, the foam 805 can be pre-stretched using a stretching station 812 including S-rolls 811 and 813. The delamination process 800 is useful for foams having low splitting forces because it has fewer components and no vacuum system.

Calendaring and creping can also be used to soften and rupture cell membranes to improve cellular connectivity, and thermoforming can be used to shape the foam absorbent. Mechanical, hydraulic, and thermal perforation can also be used to soften foam and further increase open-cell content.

Post-densification of the foam structure, after extrusion, can be employed to enhance functionality. The integrated hybrid foam layer can then be laminated to other layers, or used alone, resulting in structures having various functionalities. Various foregoing techniques can be employed to make an integrated hybrid foam layer that is receptive to printing using non-solvent flexographic inks on the open surface.

A wide variety of foam compositions are useful for preparing the integrated hybrid foam layer. Exemplary thermoplastic foam compositions are described in detail in U.S. Patent Application Publication 2005/0124709 A1, published on 9 Jun. 2005, the disclosure of which is incorporated by reference. Pertinent details are provided as follows.

In one embodiment, the foam polymer composition may include one or more surfactants and a plasticizing agent in combination with a base resin. The amount of surfactant and/or plasticizing agent can be adjusted in order to control softness, open-cell content, and cellular size and structure of the resulting foam. A thermoplastic elastomer can be added to the foam polymer composition in addition to, or in place of, the plasticizing agent to enhance the resiliency, flexibility, softness, and elasticity of the resulting foam.

The base resin, or starting material, included in the foam composition can include any suitable thermoplastic polymer, or blend of thermoplastic polymers, or blend of thermoplastic and non-thermoplastic polymers.

Examples of polymers, suitable for use as base resins, include styrene polymers, such as polystyrene or polystyrene copolymers or other alkenyl aromatic polymers; polyolefins including homo or copolymers of olefins, such as polyethylene, polypropylene, polybutylene, etc.; polyesters, such as polyalkylene terephthalate; and combinations thereof. A commercially available example of polystyrene resin is Dow STYRON® 685D, available from Dow Chemical Company in Midland, Mich., U.S.A.

Coagents and compatibilizers can be utilized for blending the base resins. Crosslinking agents can also be employed to enhance mechanical properties, foamability and expansion. Crosslinking may be done by several means including electron beams or by chemical crosslinking agents including organic peroxides. Use of polymer side groups, incorporation of chains within the polymer structure to prevent polymer crystallization, lowering of the glass transition temperature, lowering a given polymer's molecular weight distribution, adjusting melt flow strength and viscous elastic properties including elongational viscosity of the polymer melt, block copolymerization, blending polymers, and use of polyolefin homopolymers and copolymers have all been used to improve foam flexibility and foamability. Homopolymers can be engineered with elastic and crystalline areas. Syndiotactic, atactic, and isotactic polypropylenes, blends of such and other polymers can also be utilized. Suitable polyolefin resins include low, including linear low, medium and high-density polyethylene and polypropylene, which are normally made using Ziegler-Natta or Phillips catalysts and are relatively linear; generally more foamable are resins having branched polymer chains. Isotactic propylene homopolymers and blends are made using metallocene-based catalysts. Olefin elastomers are included.

Ethylene and α-olefin copolymers, made using either Ziegler-Natta or a metallocene catalyst, can produce soft, flexible foam having extensibility. Polyethylene cross-linked with α-olefins and various ethylene ionomer resins can also be utilized. Use of ethylene-vinyl acetate copolymers with other polyolefin-type resins can produce soft foam. Common modifiers for various polymers can also be reacted with chain groups to obtain suitable functionality. Suitable alkenyl aromatic polymers include alkenyl aromatic homopolymers and copolymers of alkenyl aromatic compounds and copolymerizable ethylenically unsaturated comonomers, including minor proportions of non-alkenyl aromatic polymers and blends of such. Ionomer resins can also be utilized.

Other polymers that may be employed as base resins and thermoplastic elastomers include natural and synthetic organic polymers including cellulosic polymers, methyl cellulose, polylactic acids, polyvinyl acids, polyacrylates, polycarbonates, starch-based polymers, polyetherimides, polyamides, polyesters, polymethylmethacrylates, and copolymer/polymer blends. Rubber-modified polymers such as styrene elastomers, styrene/butadiene copolymers, ethylene elastomers, butadiene, and polybutylene resins, ethylene-propylene rubbers, EPDM, EPM, and other rubbery homopolymers and copolymers of such can be added to enhance softness and hand. Olefin elastomers can also be utilized for such purposes. Rubbers, including natural rubber, SBR, polybutadiene, ethylene propylene terpolymers, and vulcanized rubbers, including TPVs, can also be added to improve rubber-like elasticity.

Thermoplastic foam absorbency can be enhanced by foaming with spontaneous hydrogels, commonly known as superabsorbents. Superabsorbents can include alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile grafted starch, acrylic acid grafted starch, carboxy-methyl-cellulose, isobutylene maleic anhydride copolymers, and mixtures thereof. Further suitable polymers include inorganic polymers, such as polyphosphazene, and the like. Furthermore, thermoplastic foam biodegradability and absorbency can be enhanced by foaming with cellulose-based and starch-based components such as wood and/or vegetable fibrous pulp/flour.

The foam polymer composition may also, or alternatively, include diblock, triblock, tetrablock, or other multi-block thermoplastic elastomeric and/or flexible copolymers such as polyolefin-based thermoplastic elastomers including random block copolymers including ethylene α-olefin copolymers; block copolymers including hydrogenated butadiene-isoprene-butadiene block copolymers; stereoblock polypropylenes; graft copolymers, including ethylene-propylene-diene terpolymer or ethylene-propylene-diene monomer (EPDM), ethylene-propylene random copolymers (EPM), ethylene propylene rubbers (EPR), ethylene vinyl acetate (EVA), and ethylene-methyl acrylate (EMA); and styrenic block copolymers including diblock and triblock copolymers such as styrene-isoprene-styrene (SIS), styrene-butadiene-styrene (SBS), styrene-isoprene-butadiene-styrene (SIBS), styrene-ethylene/butylene-styrene (SEBS), or styrene-ethylene/propylene-styrene (SEPS), which may be obtained from Kraton Polymers of Belpre, Ohio, U.S.A., under the trade designation KRATON® elastomeric resin or from Dexco, a division of ExxonMobil Chemical Company in Houston, Tex., U.S.A., under the trade designation VECTOR® (SIS and SBS polymers) or SEBS polymers as the SEPTON® series of thermoplastic rubbers from Kuraray America, Inc. in New York, N.Y., U.S.A. The foam polymer composition may include blends of thermoplastic elastomers with dynamic vulcanized elastomer-thermoplastic blends; thermoplastic polyether ester elastomers; ionomeric thermoplastic elastomers; thermoplastic elastic polyurethanes, including those available from E.I. Du Pont de Nemours in Wilmington, Del., U.S.A., under the trade name LYCRA® polyurethane, and ESTANE® available from Noveon, Inc. in Cleveland, Ohio, U.S.A.; thermoplastic elastic polyamides, including polyether block amides available from ATOFINA Chemicals, Inc. in Philadelphia, Pa., U.S.A., under the trade name PEBAX® polyether block amide. The foam polymer composition may include thermoplastic elastic polyesters, including those available from E.I. Du Pont de Nemours Company, under the trade name HYTREL®, and ARNITEL® from DSM Engineering Plastics of Evansville, Ind., U.S.A., and single-site or metallocene-catalyzed polyolefins having a density of less than about 0.89 grams/cubic centimeter such as metallocene polyethylene resins, available from Dow Chemical Company in Midland, Mich., U.S.A. under the trade name AFFINITY™; polyethylene-based elastomers from ExxonMobil Chemical Co. of Houston, Tex., U.S.A under the trade name EXACT™; and combinations thereof.

As used herein, a tri-block copolymer has an ABA structure where the A represents several repeat units of type A, and B represents several repeat units of type B. As mentioned above, several examples of styrenic block copolymers are SBS, SIS, SIBS, SEBS, and SEPS. In these copolymers the A blocks are polystyrene and the B blocks are the rubbery component. Generally these triblock copolymers have molecular weights that can vary from the low thousands to hundreds of thousands and the styrene content can range from 5% to 75% based on the weight of the triblock copolymer. A diblock copolymer is similar to the triblock but is of an AB structure. Suitable diblocks include styrene-isoprene diblocks, which have a molecular weight of approximately one-half of the triblock molecular weight and having the same ratio of A blocks to B blocks. Diblocks with a different ratio of A to B blocks or a molecular weight larger or greater than one-half of triblock copolymers may be suitable for improving the foam polymer formula for producing low-density, soft, flexible, absorbent foam via polymer extrusion.

It may be particularly beneficial to include a thermoplastic elastomer having a high diblock content and high molecular weight as part of the foam polymer formula to extrude low-density, soft, flexible, resilient, absorbent, thermoplastic foam. For example, the thermoplastic elastomer may have a diblock content between about 50% and about 80%, by weight, of the total thermoplastic elastomer weight.

KRATON® products, available from KRATON Polymers LLC, have been shown to act as a discontinuous phase in styrenic-based foams and act as cell-opener generators when used in small amounts. The amount of KRATON® polymers used in the foam polymer composition as a whole is of such a large magnitude that the cell-opener effect is negligible compared to the resiliency, flexibility, elasticity, and softness imparted.

Suitably, the foam polymer composition includes up to about 90% by weight of polystyrene, and at least 10% by weight of thermoplastic elastomer. More particularly, the foam polymer composition may include between about 45% and about 90% by weight of polystyrene, and between about 10% and about 55% by weight of thermoplastic elastomer. Alternatively, the foam polymer composition may include between about 50% and about 80% by weight of polystyrene, and between about 20% and about 50% by weight of thermoplastic elastomer. In one embodiment, for example, the foam polymer composition may include equal amounts of polystyrene and thermoplastic elastomer.

In another embodiment, the foam polymer composition may include about 40% to about 80% by weight polystyrene and about 20% to about 60% by weight thermoplastic elastomer. In another embodiment, the foam polymer composition may include about 50% to about 70% by weight polystyrene and about 30% to about 50% by weight thermoplastic elastomer.

A plasticizing agent can be included in the foam polymer composition. A plasticizing agent is a chemical agent that imparts flexibility, stretchability and workability. The type of plasticizing agent has an influence on foam gel properties, blowing agent migration resistance, cellular structure, including the fine cell size, and number of open cells. Typically plasticizing agents are of low molecular weight. The increase in polymer chain mobility and free volume caused by incorporation of a plasticizing agent typically results in a Tg decrease, and plasticizing agent effectiveness is often characterized by this measurement. Petroleum-based oils, fatty acids, and esters are commonly used and act as external plasticizing agents or solvents because they do not chemically bond to the polymer yet remain intact in the polymer matrix upon crystallization.

The plasticizing agent increases cell connectivity by thinning membranes between cells to the point of creating porous connections between cells; thus, the plasticizing agent increases open-cell content. Suitably, the plasticizing agent is included in an amount between about 0.5% and about 10%, or between about 1% and about 10%, by weight, of the foam polymer composition. The plasticizing agent is gradually and carefully metered in increasing concentration into the foam polymer formula during the foaming process because too much plasticizing agent added at once creates cellular instability, resulting in cellular collapse.

Examples of suitable plasticizing agents include polyethylene, ethylene vinyl acetate, mineral oil, palm oil, waxes, esters based on alcohols and organic acids, naphthalene oil, paraffin oil, and combinations thereof. A commercially available example of a suitable plasticizing agent is a small-chain polyethylene that is produced as a catalytic polymerization of ethylene; because of its low molecular weight it is often referred to as a "wax." This low-density, highly branched polyethylene "wax" is available from Eastman Chemical Company of Kingsport, Tenn., U.S.A., under the trade designation EPOLENE® C-10.

In order for the foam to be used in personal care and medical absorbent applications and many absorbent wiping articles and non-personal care articles, the foam must meet stringent chemical and safety guidelines. A number of plasticizing agents are FDA-approved. These plasticizing agents include: acetyl tributyl citrate; acetyl triethyl citrate; p-tert-butylphenyl salicylate; butyl stearate; butylphthalyl butyl glycolate; dibutyl sebacate; di-(2-ethylhexyl) phthalate; diethyl phthalate; diisobutyl adipate; diisooctyl phthalate; diphenyl-2-ethylhexyl phosphate; epoxidized soybean oil; ethylphthalyl ethyl glycolate; glycerol monooleate; monoisopropyl citrate; mono-, di-, and tristearyl citrate; triacetin (glycerol triacetate); triethyl citrate; and 3-(2-xenoyl)-1,2-epoxypropane.

In certain embodiments, the same material used as the thermoplastic elastomer may also be used as the plasticizing agent. For example, the KRATON® polymers, described above, may be used as a thermoplastic elastomer and/or a plasticizing agent. In this case, the foam polymer formula may include between about 10% and about 50% by weight of a single composition that acts as both a thermoplastic elastomer and a plasticizing agent. Described in an alternative manner, the foam may be formed without a plasticizing agent per se; in which case, the foam polymer formula may include between about 10% and about 50% by weight of the thermoplastic elastomer.

Foaming of soft, flexible polymers, such as thermoplastic elastomers, to a low density is difficult to achieve. The addition of a plasticizing agent makes foaming to low densities even more difficult to achieve. The use of a surfactant in the foam polymer composition helps to overcome this difficulty. The surfactant stabilizes the cells, thereby counteracting cellular collapse while retaining an open-cell structure. This stabilization of the cells creates cell uniformity and control of cell structure. In addition to enabling foaming of plasticized thermoplastic elastomer polymer containing foam formulations to low densities, the surfactant also provides wettability to enable the resulting foam to absorb fluid.

While it is not intended to limit the invention to a particular theory, it is believed that improved cell stabilization is achieved via the use of surfactant in a foam polymer formula containing a plasticizing agent. The addition of a plasticizing agent makes foaming to low densities even more difficult to achieve. Plasticizing agents such as waxes, oils, silicone defoamers, and small particulates at low addition provide localized surface tension reduction in the foam cell membrane, which causes rupturing and premature cellular collapse or coalescence. The addition of a surfactant in the foam polymer composition counteracts thermodynamic and kinetic instabilities of bubble formation in the polymer melt. The surfactant stabilizes the cells, thereby counteracting cellular collapse caused by the plasticizing agent. This stabilization of the cells creates cell uniformity in terms of cell size and cell size distribution and thereby allows control of cell structure. Since the surfactant is a surface active agent, it lowers the surface or interfacial tension and thus assists bubble formation. A decreased surface tension reduces the pressure differential required to maintain a bubble of a certain size, reduces the pressure difference between bubbles of different sizes, reduces the free energy required to maintain a given interfacial area, and thus increases the bubble nucleation rate. As Gibbs theorem explains, a surfactant combats excessive thinning of cell membranes and restores surfactant concentration to the surface and thereby acts as a stabilizing factor; however, a surfactant does not restore liquid to the film, which results in a lack of self-repair. The Marangoni effect describes surface flow of dragging underlying layers of liquid to restore film thickness, which enhances film elasticity and resilience and thus counters cellular coalescence. This again is a stabilizer. Assuming the credence of these two mechanisms, a surfactant would be most effective if it is designed so that the Marangoni effect dominates the foam polymer formula, for if the Gibbs effect dominates, the diffusion rate would be too high and self-repair would not occur. Therefore the addition of surfactant acts as a "buffer" or "stabilizer" to control surface tension and with control of temperature, which also affects surface tension, melt viscosity and melt strength, bubble stability can occur so that cells form in the thermoplastic melt. This effect is offset by lowering the surface tension forces that hold the polymer matrix together.

Bubble walls typically drain due to gravity and capillary forces. Such drainage thins the walls before the cell struts are sufficiently hardened, which leads to cell collapse. La Place and Young proposed that capillary pressure at the junction of two or more ribs is lower, thereby creating flow from the membrane to the ribs and, consequently, thinning. With a sufficient amount of surfactant molecules arranged preferentially to migrate to the surface of the film membrane, the presence of surfactant at the membrane's thin film surfaces provides resistance to drainage of the molten plastic. If the film layer is sufficiently thick, such as in a foam membrane, it can be further stabilized by an ionic double layer of molecules resulting from orientation of ionic surfactants. Both nonionic and ionic surfactants can exhibit another stabilizing force if the membrane is sufficiently thin. This would be done by the alignment of surfactant tails to create a bi-layer structure, such as found in biological cells, that is held together via Van der Waals forces and thus stabilizes the foam membrane.

(References: *Polymeric Foams*, edited by Daniel Klempner and Kurt Frisch, Hanser Publishers, 1991; and *Foam Extrusion*, edited by S. T. Lee, Technomic Publishing Co., Inc., 2000.)

The surfactant is thought to also provide resistance to diffusion of the gas from the cell to the surroundings, which also aids in resisting collapse. The reduced gas permeability due to the drainage resistance is related to the degree the surfactant can pack into the bubble's film surface and explains the difference between the performances of the various surfactants. This reduced rate of diffusion allows sufficient cooling for strut formation to prevent coalescence. This reduced rate of diffusion allows sufficient cooling for strut formation to prevent coalescence. The surfactant does not need to prevent drainage, but simply slows it sufficiently so that the cell struts are substantially hardened thereby preventing cell coalescence. In general terms, it is expected that surfactants that are highly mobile in the melt, highly surface active, and can pack tightly and prevent membrane drainage will provide the best cell stabilization.

The surfactant may be a single surfactant, or a multi-component surfactant system. A multi-component surfactant system is a combination of two or more surfactants. It has been found that certain multi-component surfactant systems can achieve equal or better foam formation at a lower dosage than certain single-component surfactant systems.

The polymer melt can be continuously extruded to form a soft, flexible, open-cell, thermoplastic, absorbent foam. As explained above, the open-cell content of the foam is controlled by adjusting the amounts of plasticizing agent and surfactant. Open-cell content can be measured using a gas pycnometer according to ASTM D2856, Method C. The open-cell content of the resulting foam is suitably about 50% or greater, or about 70% or greater, or about 80% or greater.

The surfactant can be included in the foam polymer composition in an amount between about 0.05% and about 10%, or between about 0.1% and about 5%, by weight. In an embodiment in which the surfactant is a multi-component surfactant system, the total of all surfactants can be included in the foam polymer composition in an amount between about 0.05% and about 8.0%, or between about 0.1% and about 3.0%, by weight. Examples of suitable surfactants include cationic, anionic, amphoteric, and nonionic surfactants. Anionic surfactants include the alkylsulfonates. Examples of commercially available surfactants include HOSTASTAT® HS-1, available from Clariant Corporation in Winchester, Va., U.S.A.; Cognis EMEREST® 2650, Cognis EMEREST® 2648, and Cognis EMEREST® 3712, each available from Cognis Corporation in Cincinnati, Ohio, U.S.A.; and Dow Corning 193, available from Dow Chemical Company in Midland, Mich., U.S.A. Alkyl sulfonates are quite effective; however, use of this class of surfactants in certain applications may be limited because of product safety. Some combinations offer unexpected benefits where the alkyl sulfonate is added at a substantially lower level in conjunction with another surfactant to yield good foaming and wettability. In one embodiment, for example, the surfactant can be added to the foam polymer composition in a gaseous phase, such as through the use of a blowing agent such as supercritical carbon dioxide. One benefit of using a gaseous surfactant is that the surfactant can fully penetrate and be incorporated into the polymer matrix, which can improve substantivity and thereby reduce surfactant fugitivity to enhance the foam's permanent wettability.

The balance between cell stabilization of the surfactant and the enhanced melt drainage from the plasticizing agent enables control over the open-cell content of the resulting foam. More particularly, the amount of surfactant can be adjusted to counteract the effects of the plasticizing agent, and/or the amount of the plasticizing agent can be adjusted to counteract the effects of the surfactant. For example, if the plasticizing agent is included in the foam polymer composition in an amount between about 0.5% and about 5% by weight, then the surfactant should be included in the foam polymer composition in an amount between about 0.5% and about 5% by weight. Similarly, if the plasticizing agent is included in the foam polymer composition in an amount between about 5% and about 10% by weight, then the surfactant should be included in the foam polymer composition in an amount between about 2% and about 10% by weight. In addition, the polymer resin melt flow index can be adjusted to offset the plasticizing agent's effect.

Other additives can be included in the foam polymer composition to enhance the properties of the resulting foam. As described above, a nucleant can be added to improve foam gas bubble formation in the foam polymer composition. Examples of suitable nucleants include talc, magnesium carbonate, nanoclay, silica, calcium carbonate, modified nucleant complexes, and combinations thereof. An example of a commercially available nucleant is a nanoclay available under the trade name CLOISITE® 20A, from Southern Clay Products, Inc. in Gonzales, Tex., U.S.A. The nucleant can be added to the foam polymer composition in an amount between about 0.1% and about 5% by weight. Nucleants, or nucleating agents, are described in greater detail below.

A blowing agent, described in greater detail above, can be added to the foam polymer composition to aid in the foaming process. Blowing agents can be compounds that decompose at extrusion temperatures to release large volumes of gas, volatile liquids such as refrigerants and hydrocarbons, or ambient gases such as nitrogen and carbon dioxide, or water, or combinations thereof. A blowing agent can be added to the foam polymer composition in an amount between about 1% and about 10% by weight.

Once the foam polymer formula is mixed and formed, including the plasticizing agent, the surfactant, and any other additives, the foam polymer composition is heated and mixed, suitably to a temperature between about 100 and about 500 degrees Celsius, to create a polymer melt. The plasticizing agent reduces elongational viscosity of the polymer melt, which leads to foaming difficulties. However, the surfactant mediates the impact of the plasticizing agent on the viscosity, thereby providing control over the open-cell content of the resulting foam. Also, as mentioned, the polymer resin melt index can be adjusted to offset the plasticizing agent's effect.

The polymer melt can be foamed using any suitable foaming technique known to those skilled in the art. The density of the open-celled foam is suitably about 0.35 $g/cm^3$ or less, or about 0.20 $g/cm^3$ or less, or about 0.10 $g/cm^3$ or less, for example, about 0.02 to about 0.10 $g/cm^3$. Foam expansion ratio is generally about 10 or greater. Suitably, the absorbent foam has about 5% or more closed cells, or about 10% or more closed cells, or about 15% or more closed cells to improve resiliency and/or compression resistance.

The hybrid absorbent foam, and its integrated hybrid foam layer, can also be characterized in terms of various additional properties. As explained above, the open-cell content of the foam, which can be controlled by adjusting the amount of surfactant and/or plasticizing agent included in the foam polymer formula, is suitably about 50% or greater, or about 60% greater, or about 70% or greater, or about 80% or greater, as measured using ASTM D2856. The foam may also include about 5% or more, or about 10% or more, or about 15% or more closed cells to improve resiliency and/or compression resistance. The foam is low density, with a density of about 0.10 gram/cubic centimeter ($g/cm^3$) or less, or about 0.07 $g/cm^3$ or less, or about 0.04 $g/cm^3$ or less and suitably at least about 0.02 $g/cm^3$ (before any compression is applied to meet specific packaging and/or in-use requirements), is soft and flexible, and is resilient and elastic with an edge compression of about 250 grams or less, or about 100 grams or less, or about 35 grams or less. The foam density is a measurement of bulk density, determined using ASTM D1622. Edge compression can be measured using the Edge Compression Test Method, which is described in detail below. Softness, flexibility, elasticity, and resiliency are also demonstrated through compression set resistance. The foam of the invention suitably has a compression resistance of about 20% compression set or less, or about 15% compression set or less, or about 7% compression set or less, as measured using ASTM D3575.

The hybrid absorbent thermoplastic foam is soft and flexible. The hybrid absorbent foam and the integrated hybrid foam layer have a bending modulus of less than 6000 KPa at 1 mm deflection, suitably less than 4000 KPa, or less than 2000 KPa, using the Bending Modulus Test described herein.

Due to surface texturing (described above), the integrated hybrid foam layer may, on its open surface, have a surface roughness of about 40 to about 350 microns, suitably about 40 to about 80 microns for lightly textured samples and about 300 to about 350 microns for heavily textured samples, measured using noncontact optical profilometry as described below. These represent ranges to produce excellent tactile aesthetics of soft absorbent thermoplastic foams.

The integrated hybrid foam layer remains suitably absorbent even after repeated washings. The surfactant permanence remains intact in the foam such that about 15% or less, or about 10% or less, or about 5% or less of the surfactant is washed off after soaking in water for 24 hours. The Surfactant Permanence Test is described in detail below. An alternative measure of the surfactant permanence is the surface tension of the supernatant in the same Surfactant Permanence Test. More particularly, the surface tension of the supernatant remains greater than about 40 dynes/centimeter, or greater than about 50 dynes/centimeter, or greater than about 60 dynes/centimeter.

The integrated hybrid foam layer with 0.9% NaCl saline solution has a saturated capacity of about 1 gram/gram (g/g) or greater, or about 15 g/g or greater, or about 30 g/g or greater, as measured under a 0.5 psi (3.45 KPa) load using the Saturated Capacity Test Method, described in detail below, and a fluid intake flux of about 1 ml/sec/$in^2$ (0.15 ml/sec/$cm^2$) or greater, or about 3 ml/sec/$in^2$ (0.46 ml/sec/$cm^2$) or greater, or about 5 ml/sec/$in^2$ (0.77 ml/sec/$cm^2$) or greater upon the first insult, about 1 ml/sec/$in^2$ (0.15 ml/sec/$cm^2$) or greater, or about 3 ml/sec/$in^2$ (0.46 ml/sec/$cm^2$) or greater, or about 5 ml/sec/$in^2$ (0.77 ml/sec/$cm^2$) or greater upon the second insult, and about 1 ml/sec/$in^2$ (0.15 ml/sec/$cm^2$) or greater, or about 3 ml/sec/in (0.46 ml/sec/$cm^2$) or greater, or about 5 ml/sec/in² (0.77 ml/sec/cm²) or greater upon the third insult, using the Fluid Intake Flux Test or Modified Fluid Intatke Flux Test, also described in detail below. Furthermore, the foam has a vertical wicking height of about 5 centimeters (cm) or higher, or about 7 cm or higher, or about 10 cm or higher, or about 15 cm or higher in 30 minutes, as measured with 0.9% NaCl saline solution using the Vertical Wicking Test, also described in detail below.

The integrated hybrid foam layer may have a vertical wicking fluid flux at zero height of at least about 5 g/sec/m², or at least about 7 g/sec/m², or at least about 10 g/sec/m², measured using the Vertical Wicking Fluid Flux Test described herein. The foam may have a functional capacity greater than about 0.1 gram/cc, suitably greater than about 0.4 gram/cc, or about 0.1 to about 1.0 gram/cc, measured using the Functional Capacity Test described herein.

The integrated hybrid foam layer may be thin, but possesses considerable strength. More particularly, the foam layer may have a basis weight of about 400 grams per square meter or less, with an overall bulk, measured at 0.05 psi (0.345 KPa) loading, of about 6 millimeters or less. Suitably, the foam layer has a cross-direction (CD) trap tear strength of about 300 grams or greater, or about 600 grams or greater, or about 1200 grams or greater, and a machine-direction (MD) trap tear strength of about 300 grams or greater, or about 600 grams or greater, or about 1200 grams or greater. Overall bulk can be measured using the Foam Caliper Test described herein. Trap tear MD/CD strength of the foam may be measured using ASTM D1117-14.

The integrated hybrid foam layer may have a bending modulus of less than about 6000 KPa, suitably less than about 4000 KPa, or about 200 to about 2000 KPa, at 1 mm deflection, measured using the Bending Modulus Test described herein. The foam layer may have a dry tensile strength of about 5 kg to about 15 kg, suitably about 8 kg to about 12 kg, or about 9 kg to about 10 kg, measured using the Dry Tensile Strength Test described herein. The foam layer may have a wet tensile strength of about 5 kg to about 15 kg, suitably about 7 kg to about 12 kg, or about 8.5 kg to about 10 kg, measured using the Wet Tensile Strength Test described herein. The foam layer may have a Wet Tensile Loss of less than about 10%, suitably less than about 8%, measured by comparing dry and wet tensile strengths, as described herein. The foam layer may have a static coefficient of friction of about 0.20 to about 1.50, typically about 0.40 to about 1.0, measured using the Coefficient Of Friction Test described herein.

The hybrid absorbent foam of the invention is particularly suitable for use in a variety of absorbent article applications including, without limitation, personal care absorbent articles, medical absorbent articles, and industrial absorbent articles, including without limitation, absorbent wiping articles. Personal care absorbent articles include, but are not limited to, absorbent articles such as disposable diapers, baby wipes, training pants, child-care pants, swimwear, mitts, and other disposable garments; feminine-care products including, but not limited to, sanitary napkins, wipes, menstrual pads, panty liners, panty shields, interlabials, tampons, and tampon applicators; adult-care products including, but not limited to, wipes, pads, containers, incontinence products, and urinary shields. Medical absorbent articles include professional and consumer health medical care products such as products for applying hot or cold therapy, hospital gowns, surgical drapes, mitts, gloves, bandages, wound dressings, wipes, covers, containers, filters, disposable garments and bed pads, medical absorbent garments, underpads, and the like. Absorbent wiping articles include facial tissue, washcloths, mitts, cleaning articles including sponges and wipes and impregnated wipes, towels such as kitchen towels, disposable cutting sheets, away-from-home towels, wet-wipes, bath tissue, and the like. Besides use of the hybrid absorbent foam for personal care absorbent articles, the foam can also be used in a variety of clothing components, and non-personal care absorbent products including filters, masks, packaging absorbents, trash bags, stain removers, applicator mitts for topical compositions, laundry soil/ink absorbers, detergent agglomerators, lipophilic fluid separators, cleaning devices, athletic and recreation products, and construction and packaging uses. Because the hybrid absorbent foam is thermoplastic, the foam is also recyclable. The hybrid absorbent foam can be made biodegradable by including biodegradable thermoplastic polymers in the foam composition such as polylactic acid, starches, or the like.

Test Methods

Bending Modulus Test

Figure 8A:
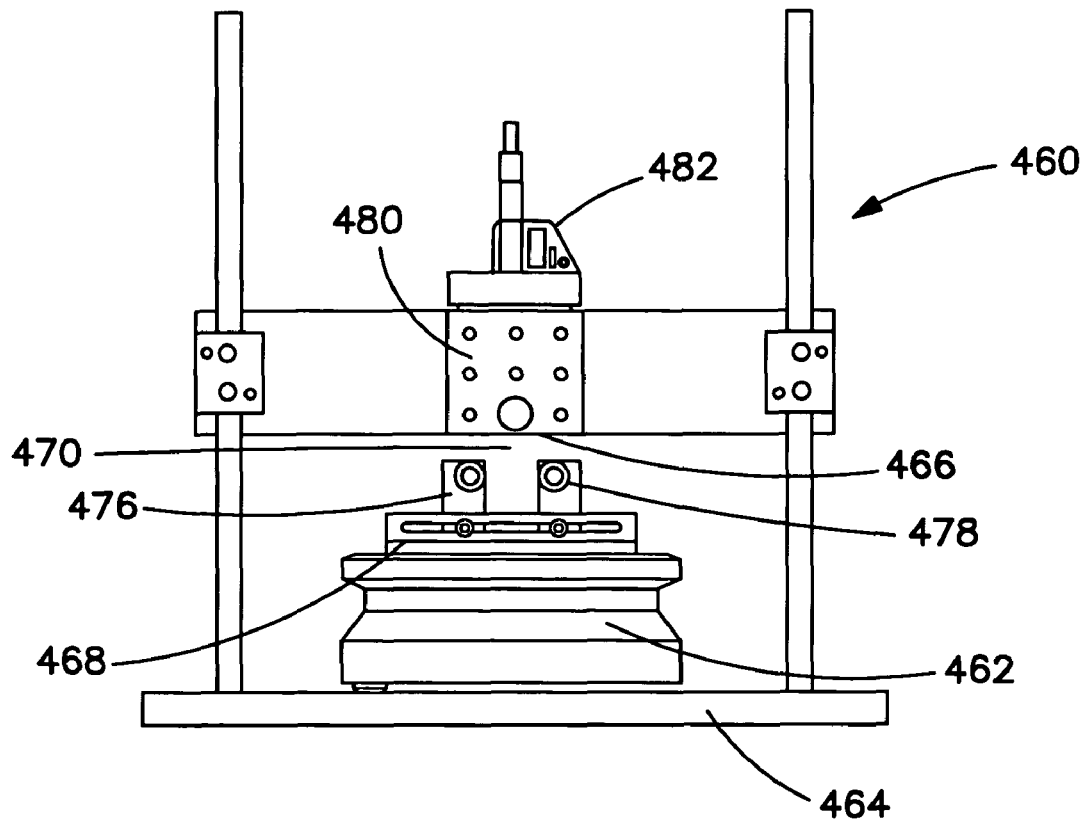
FIGS. 8A-8B schematically illustrate an apparatus used to perform the Bending Modulus Test, described herein.
Figure 8B:
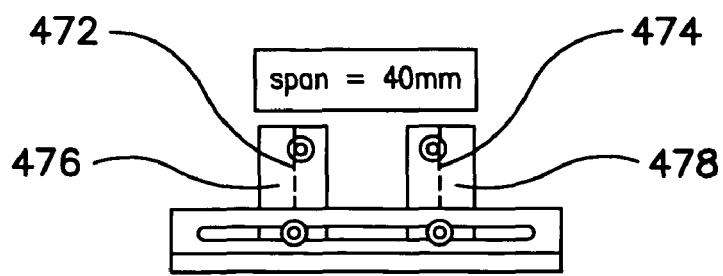

This test is similar to that described in ASTM D 5934. Samples are cut to have dimensions of 64 mm long×38 mm wide (W). The thickness of the sample (T) is then measured in millimeters. With reference to FIGS. 8A and 8B, assemble the apparatus 460 so that the balance 462 is completely on the leveled baseboard 464, and the loading nose 466 is centered over the weigh pan 468. The fixture base 470 should be inspected to be sure that the distance between the centers 472, 474 of the two 1-inch (2.54 cm) diameter cylinders 476, 478 (S) is 40 mm. The fixture base 470 should be placed on the weigh pan 468 so that the two cylinders 476, 478 are parallel with the cylinder on the loading nose 466. The caliper 482 should be adjusted to lower the assembly 480 with the loading nose 466 in order to be sure that the loading nose 466 is parallel to the bottom cylinders 476, 478. The sample (not shown) should then be laid across the bottom cylinders 476, 478 with the longer dimension along the span. The loading nose 466 should not touch the sample. At this point, the balance 462 should be tared.

Dial the caliper 482 to move assembly 480 down so that the loading nose 466 just touches the sample and the balance 462 reading (load) is 0.5 g. Then zero the caliper 482; this will be the reference point for deflection measurements. Set a timer (not shown) for 2 minutes. Dial the caliper 482 to move the loading nose 466 down to 1.0 mm distance (D) then start the timer. Record the load (F) in grams after 2 minutes, then discard the sample. The Bending Modulus (BM) at 1.0 mm deflection can be calculated in g/mm² using the following formula:

$$BM = \frac{F(S^3)}{4D(T^3)W}$$

To convert the BM to KPa, multiply the above result by 9.8.

Static Coefficient of Friction Test

Coefficient of friction was tested in accordance with ASTM D1894 using a Sintech 2/S test apparatus from MTS. The apparatus is set up as in FIG. 1 method C in ASTM D1894. Sample size is 2.5×7 inches (6.35×17.8 cm) and wrapped around the sled so that the tested side is facing out and in contact with the test surface. Glass was used as the test surface. The static coefficient of friction was calculated and an average of five samples was reported.

Dry and Wet Tensile Strength, Wet Tensile Loss

Dry and Wet tensile strength testing was conducted using the cut strip test method at constant rate of extension in accordance with ASTM D5035. The sample size was modified from the ASTM method and was equal to 3×6 inches (7.62×15.2 cm). The wet strength was carried out as specified in the ASTM method. No surfactant was added to the water during the testing. Percent wet tensile loss is the percent of tensile loss due to wetting the material. Percent wet tensile loss is calculated with the following formula:

% Wet Tensile Loss=(Dry Tensile−Wet Tensile)/Dry Tensile*100.

Foam Caliper (Bulk) Test Method

The caliper or thickness of a material, in millimeters, is measured at 0.05 PSI (0.345 KPa) using a Frazier spring model compressometer #326 bulk tester with a 2 inch (50.8 mm) foot (Frazier Precision Instrument Corporation, 925 Sweeney Drive, Hagerstown, Md., U.S.A.). Each type of sample is subjected to three repetitions of testing and the results are averaged to produce a single value.

Saturated Capacity Test Method

Saturated Capacity is determined using a Saturated Capacity (SAT CAP) tester with a Magnahelic vacuum gage and a latex dam, comparable to the following description. Referring to FIGS. 9-11, a Saturated Capacity tester vacuum apparatus 110 comprises a vacuum chamber 112 supported on four leg members 114. The vacuum chamber 112 includes a front wall member 116, a rear wall member 118 and two side walls 120 and 121. The wall members are sufficiently thick to withstand the anticipated vacuum pressures, and are constructed and arranged to provide a chamber having outside dimensions measuring 23.5 inches (59.7 cm) in length, 14 inches (35.6 cm) in width and 8 inches (20.3 cm) in depth.

A vacuum pump (not shown) operably connects with the vacuum chamber 112 through an appropriate vacuum line conduit and a vacuum valve 124. In addition, a suitable air bleed line connects into the vacuum chamber 112 through an air bleed valve 126. A hanger assembly 128 is suitably mounted on the rear wall 118 and is configured with S-curved ends to provide a convenient resting place for supporting a latex dam sheet 130 in a convenient position away from the top of the vacuum apparatus 110. A suitable hanger assembly can be constructed from 0.25 inch (0.64 cm) diameter stainless steel rod. The latex dam sheet 130 is looped around a dowel member 132 to facilitate grasping and to allow a convenient movement and positioning of the latex dam sheet 130. In the illustrated position, the dowel member 132 is shown supported in a hanger assembly 128 to position the latex dam sheet 130 in an open position away from the top of the vacuum chamber 112.

A bottom edge of the latex dam sheet 130 is clamped against a rear edge support member 134 with suitable securing means, such as toggle clamps 140. The toggle clamps 140 are mounted on the rear wall member 118 with suitable spacers 141 which provide an appropriate orientation and alignment of the toggle clamps 140 for the desired operation. Three support shafts 142 are 0.75 inches (1.90 cm) in diameter and are removably mounted within the vacuum chamber 112 by means of support brackets 144. The support brackets 144 are generally equally spaced along the front wall member 116 and the rear wall member 118 and arranged in cooperating pairs. In addition, the support brackets 144 are constructed and arranged to suitably position the uppermost portions of the support shafts 142 flush with the top of the front, rear and side wall members of the vacuum chamber 112. Thus, the support shafts 142 are positioned substantially parallel with one another and are generally aligned with the side wall members 120 and 121. In addition to the rear edge support member 134, the vacuum apparatus 110 includes a front support member 136 and two side support members 138 and 139. Each side support member measures about 1 inch (2.54 cm) in width and about 1.25 inches (3.18 cm) in height. The lengths of the support members are constructed to suitably surround the periphery of the open top edges of the vacuum chamber 112, and are positioned to protrude above the top edges of the chamber wall members by a distance of about 0.5 inch (1.27 cm).

A layer of egg crating type material 146 is positioned on top of the support shafts 142 and the top edges of the wall members of the vacuum chamber 112. The egg crate material extends over a generally rectangular area measuring 23.5 inches (59.7 cm) by 14 inches (35.6 cm), and has a depth measurement of about 0.38 inches (0.97 cm). The individual cells of the egg crating structure measure about 0.5 inch (1.27 cm) square, and the thin sheet material comprising the egg crating is composed of a suitable material, such as polystyrene. For example, the egg crating material can be McMaster Supply Catalog No. 162 4K 14, translucent diffuser panel material. A layer of 6 mm (0.25 inch) mesh TEFLON®-coated screening 148, available from Eagle Supply and Plastics, Inc., in Appleton, Wis., U.S.A., which measures 23.5 inches (59.7 cm) by 14 inches (35.6 cm), is placed on top of the egg crating material 146.

A suitable drain line and a drain valve 150 connect to bottom plate member 119 of the vacuum chamber 112 to provide a convenient mechanism for draining liquids from the vacuum chamber 112. The various wall members and support members of vacuum apparatus 110 may be composed of a suitable noncorroding, moisture-resistant material, such as polycarbonate plastic. The various assembly joints may be affixed by solvent welding, and the finished assembly of the tester is constructed to be watertight. A vacuum gauge 152 operably connects through a conduit into the vacuum chamber 112. A suitable pressure gauge is a Magnahelic differential gauge capable of measuring a vacuum of 0-100 inches of water (0-186 mmHg), such as a No. 2100 gauge available from Dwyer Instrument Incorporated in Michigan City, Ind., U.S.A.

The dry product or other absorbent structure is weighed and then placed in excess 0.9% NaCl saline solution and allowed to soak for twenty minutes. After the twenty minute soak time, the absorbent structure is placed on the egg crate material and mesh TEFLON®-coated screening of the Saturated Capacity tester vacuum apparatus 110. The latex dam sheet 130 is placed over the absorbent structure(s) and the entire egg crate grid so that the latex dam sheet 130 creates a seal when a vacuum is drawn on the vacuum apparatus 110. A vacuum of 0.5 pounds per square inch (psi) (3.45 KPa) is held in the Saturated Capacity tester vacuum apparatus 110 for five minutes. The vacuum creates a pressure on the absorbent structure(s), causing drainage of some liquid. After five minutes at 0.5 psi (3.45 KPa) vacuum, the latex dam sheet 130 is rolled back and the absorbent structure(s) are weighed to generate a wet weight.

The overall capacity of each absorbent structure is determined by subtracting the dry weight of each absorbent from the wet weight of that absorbent, determined at this point in the procedure. The 0.5 psi (3.45 KPa) SAT CAP or SAT CAP of the absorbent structure is determined by the following formula:

SAT CAP=(wet weight−dry weight)/dry weight;

wherein the SAT CAP value has units of grams of fluid/gram absorbent. For both overall capacity and SAT CAP, a minimum of four specimens of each sample should be tested and the results averaged. If the absorbent structure has low integrity or disintegrates during the soak or transfer procedures, the absorbent structure can be wrapped in a containment material such as paper toweling, for example SCOTT® paper towels manufactured by Kimberly-Clark Corporation, Neenah, Wis., U.S.A. The absorbent structure can be tested with the overwrap in place and the capacity of the overwrap can be independently determined and subtracted from the wet weight of the total wrapped absorbent structure to obtain a wet absorbent weight.

Single Drop Intake Time Test

Ten drops of test fluid are placed at random locations on a 4-inch (10.16 cm by 10.16 cm) sample of material, and the intake time is recorded, using the equipment and test procedure below. An average of the ten recorded times is reported as the single drop fluid intake time.

Equipment:
1. Test fluid is deionized water with several drops of blue food coloring in 100 ml.
2. Syringe pump was programmed to pump 0.038 ml of fluid.
3. Syringe was connected to tubing that was attached to a hematocrit glass tube with an orifice that has the size such that 0.038 ml made one drop.
4. A test stand was set up to hold the tube vertically above the material 1 cm in height.
5. Stopwatch accurate to 0.1 seconds.

Steps:
1. Start the syringe pump so that it drops one drop at a randomly chosen location on the foam.
2. As the drop contacts the test material, start a stopwatch.
3. Stop the timer when the fluid has sufficiently penetrated into the foam such that the reflection of light off the fluid is no longer visible.
4. Record the time.
5. Repeat 10 times in randomly chosen locations that are not close to previously tested locations.

Fluid Intake Flux Test

Figure 12B:
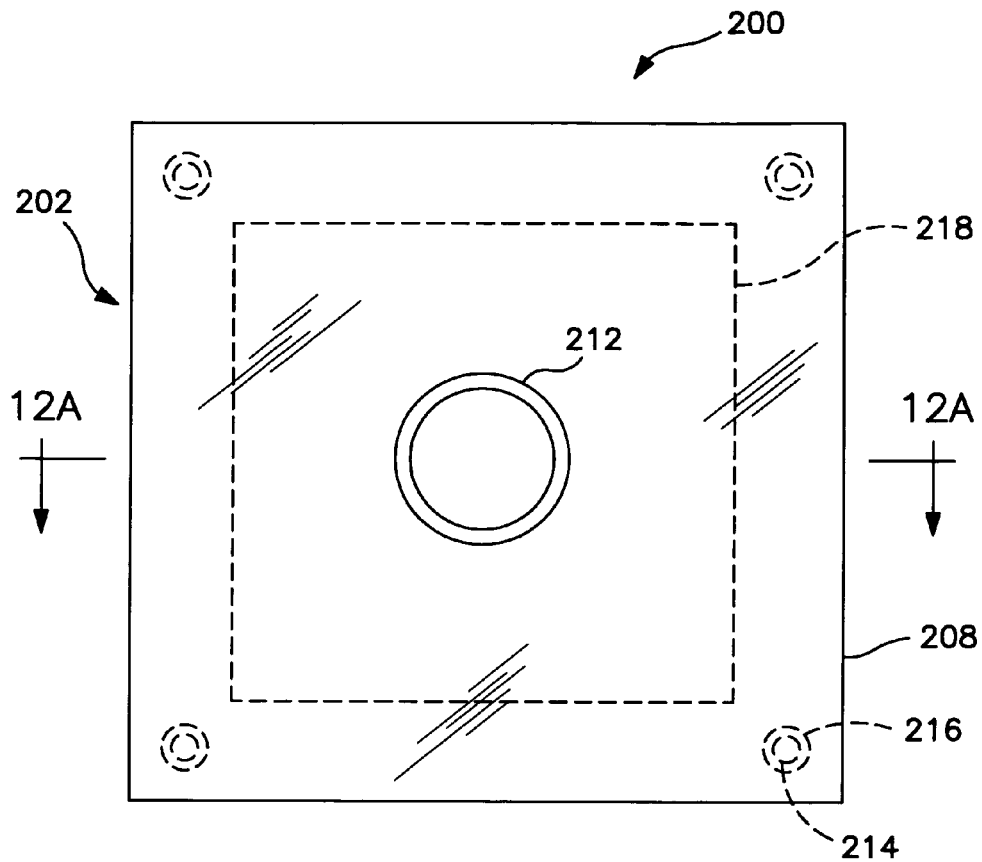
FIGS. 12A-12B representatively show a top view and a side view, respectively, of the test apparatus employed for the Fluid Intake Flux Test.
Figure 12A:
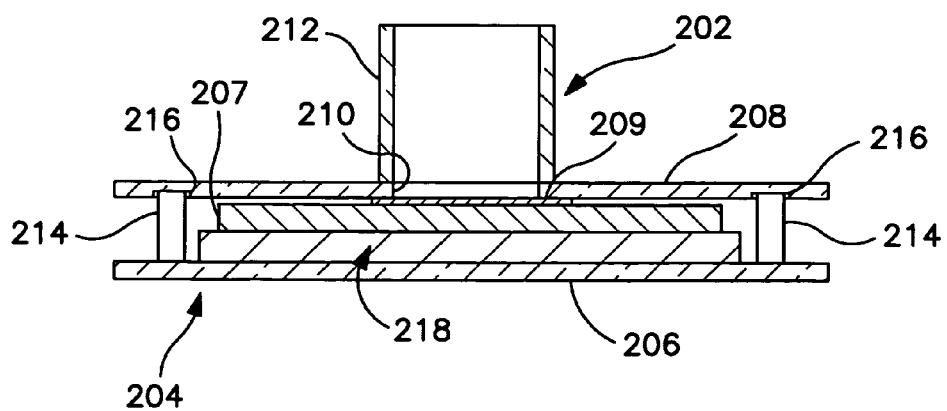

The Fluid Intake Flux (FIF) Test determines the amount of time required for an absorbent structure, and more particularly a foam sample thereof, to take in (but not necessarily absorb) a known amount of test solution (0.9 weight percent solution of sodium chloride in distilled water at room temperature). A suitable apparatus for performing the FIF Test is shown in FIGS. 12A and 12B and is generally indicated at 200. The test apparatus 200 comprises upper and lower assemblies, generally indicated at 202 and 204 respectively, wherein the lower assembly comprises a generally 7 inch (18 cm) by 7 inch (18 cm) square lower plate 206 constructed of a transparent material such as PLEXIGLAS® for supporting the absorbent foam sample during the test and a generally 4.5 inch (11.4 cm) by 4.5 inch (11.4 cm) square platform 218 centered on the lower plate 206.

The upper assembly 202 comprises a generally square upper plate 208 constructed similar to the lower plate 206 and having a central opening 210 formed therein. A cylinder (fluid delivery tube) 212 having an inner diameter of about one inch (2.54 cm) is secured to the upper plate 208 at the central opening 210 and extends upward substantially perpendicular to the upper plate. For flux determination, the inside dimension of the fluid delivery tube should maintain a ratio between 1:3 and 1:6 of the sample diameter. The central opening 210 of the upper plate 208 should have a diameter at least equal to the inner diameter of the cylinder 212 where the cylinder 212 is mounted on top of the upper plate 208. However, the diameter of the central opening 210 may instead be sized large enough to receive the outer diameter of the cylinder 212 within the opening so that the cylinder 212 is secured to the upper plate 208 within the central opening 210.

Pin elements 214 are located near the outside corners of the lower plate 206, and corresponding recesses 216 in the upper plate 208 are sized to receive the pin elements 214 to properly align and position the upper assembly 202 on the lower assembly 204 during testing. The weight of the upper assembly 202 (e.g., the upper plate 208 and cylinder 212) is approximately 360 grams to simulate approximately 0.11 pounds/square inch (psi) (0.758 KPa) pressure on the absorbent foam sample during the FIF Test.

To run the FIF Test, an absorbent foam sample 207 being three inches in diameter is weighed and the weight is recorded in grams. The foam sample 207 is then centered on the platform 218 of the lower assembly 204. To prevent unwanted foam expansion into the central opening 210, centered on top of the foam sample 207, is positioned an approximately 1.5 inch diameter piece of flexible fiberglass standard 18×16 mesh window insect screening 209, available from Phifer Wire Products, Inc., Tuscaloosa, Ala., U.S.A. The upper assembly 202 is placed over the foam sample 207 in opposed relationship with the lower assembly 204, with the pin elements 214 of the lower plate 206 seated in the recesses 216 formed in the upper plate 208 and the cylinder 212 is generally centered over the foam sample 207. Prior to running the FIF test, the aforementioned Saturated Capacity Test is measured on the foam sample 207. Thirty-three percent (33%) of the saturation capacity is then calculated; e.g., if the test foam has a saturated capacity of 12 g of 0.9% NaCl saline test solution/g of test foam and the three inch diameter foam sample 207 weighs one gram, then 4 grams of 0.9% NaCl saline test solution (referred to herein as a first insult) is poured into the top of the cylinder 212 and allowed to flow down into the absorbent foam sample 207. A stopwatch is started when the first drop of solution contacts the foam sample 207 and is stopped when the liquid ring between the edge of the cylinder 212 and the foam sample 207 disappears. The reading on the stopwatch is recorded to two decimal places and represents the intake time (in seconds) required for the first insult to be taken into the absorbent foam sample 207.

A time period of fifteen minutes is allowed to elapse, after which a second insult equal to the first insult is poured into the top of the cylinder 212 and again the intake time is measured as described above. After fifteen minutes, the procedure is repeated for a third insult. An intake flux (in milliliters/second) for each of the three insults is determined by dividing the amount of solution (e.g., four grams) used for each insult by the intake time measured for the corresponding insult. The intake rate is converted into a fluid intake flux by dividing by the area of the fluid delivery tube, i.e., 0.79 in$^2$ (5.1 cm$^2$).

At least three samples of each absorbent test foam is subjected to the FIF Test and the results are averaged to determine the intake time and intake flux of the absorbent foam.

Modified Fluid Intake Flux (FIF) Test for Smaller Foam Samples

The test is done in a similar same manner as described in the aforementioned standard Fluid Intake Flux (FIF) test; however, this test was modified to accommodate smaller samples and yet keep the same fluid delivery tube to sample size ratio as in the standard FIF test. The modifications included installing the small sample of non-swelling foam that is to be tested into a suitable holder and using a suitable fluid delivery tube. The suitable holder can be an inverted laboratory glass funnel having a uniform diameter cylindrical output tube of one inch long that rests on top of an adjustable lab jack platform positioned for downward gravitational flow. The foam, of sufficient diameter (between 0.18 inch and 0.36 inch, or between 0.46 cm and 0.91 cm) and one inch (2.54 cm) in length, is gently positioned into the top of the uniform diameter glass tube of the inverted funnel that is sufficient in size to hold the foam without significant compression so that one end faces vertically up (proximal end) and the other end is facing downward (distal end). The glass tube holds the foam in a stationary position and is sufficient in length to hold the foam sample yet then immediately enlarges to the funnel opening to avoid discharging flow complications of excess fluid after the fluid leaves the foam's distal end. A fluid delivery tube is constructed with a 0.06 inch (0.15 cm) diameter orifice and a throat length that enlarges to a diameter enabling easy dispensation of fluid into the tube. The enlargement occurs at an approximately 0.25 inch (0.64 cm) length upstream of the orifice. The fluid delivery tube is positioned directly above the proximal end of the foam sample and the inverted funnel and the foam sample is raised using the lab jack such that the fluid delivery tube is brought into contact with the foam. Afterwards, similar to the standard FIF test, thirty-three percent (33%) of the saturation capacity for the foam sample is then calculated and this volume of 0.9% NaCl saline solution is dispensed using a PIPETMAN® P-200 µl pipette, available from Gilson, Inc. in Middleton, Wis., U.S.A., or similar pipette, into the fluid delivery tube which measures 0.06 inches (0.15 cm) in discharge orifice diameter, as opposed to a 1-inch (2.54 cm) diameter as described in the standard FIF Test, and the rate of flow is measured with a stopwatch as earlier described. The preference is to utilize the earlier described standard FIF test rather than the Modified FIF test and, if discrepancies exist, the standard FIF test is relied upon.

Vertical Wicking Test Method

A sample of foam is cut and mounted so that it hangs in a vertical orientation to gravity with an exposed foam edge in a substantially horizontal orientation. A sufficiently large reservoir of 0.9% NaCl saline test solution is raised, using a standard lab jack, so that the foam's horizontal edge extends approximately two millimeters beneath the surface of the saline. A timer is started simultaneous to the penetration of the foam into the saline. After thirty minutes, the height of the fluid in the foam is measured relative to the surface of the saline. If desired, the saline can contain a non-surface active, non-chromatographic dye to aid in identifying the penetration and wicking of the test fluid within the foam. Alternatively, the foam may be marked at the surface of the fluid and the fluid reservoir lowered to remove further contact with the foam. To compensate for possible foam expansion upon hydration, the foam may be marked at the fluid surface after the wicking time. Measurement of the fluid height in the foam using the initial foam dimensions may be done via appropriate means including x-ray imaging, optical measurement, or slicing sections of the foam until 0.9% NaCl saline test solution is apparent in the slice.

Open Area Test

The open area test is an image analysis for measuring the open area of a foam surface. The foam surface is colored with a dark pigment using a black permanent marker. A magnified image of the surface is acquired with transmitted light using standard microscopy. The pigmented surface creates enough image contrast between open and closed areas that standard image analysis software can quantify the total surface area and the area of the open portions. This technique can be employed whether the open surface is due to microaperturing, microslitting, areal splitting, or any other technique. If the open surface is caused by areal splitting, then the open surface area is similar to the open-cell content at the surface.

If the open surface is caused by microaperturing, microslitting, or some other post-treatment technique besides areal splitting, then the post-treatment process conditions are adjusted to ensure that the apertures or other openings are deep enough to penetrate into the open-cell portion of the integrated hybrid foam layer without penetrating the closed surface on the opposing side of the foam. The depth of penetration required, as well as the depth of a particular opening in a post-treatment foam, can be determined using scanning electron microscopy ("SEM") of a cross-section of the integrated hybrid foam layer, and the following procedure:

1. Take an SEM of the cross section.
2. Using image analysis, quantify the center of each cell.
3. Optically determine (by user determination) which cells are open, and which are closed.
4. Generate a graph that shows the number % of open cells/total cells as a function of position (depth).
5. Call the boundary the location where the open-cell percentage exceeds 50%.

Surface Roughness Test

Noncontact optical profilometry was used to determine the average surface roughness of both sides of two representative hybrid absorbent foams of the invention. Data was collected using a FRT MicroProf® profilometer.

A 10-mm×10-mm area of each sample was analyzed. Comparisons were made between a) untextured samples, b) lightly textured samples, and c) heavily textured samples. Data spacing was 10-microns based on 1000 lines×1000 points/line sampled over the 10 mm area. Vertical resolution with the 1 mm z-range optical sensor is better than 100-nanometers (0.1 µm).

The average surface roughness parameter (sPa) is calculated as the arithmetic average of the absolute deviations about the least squares (LSQ) best-fit plane through the data. It is the most widely used measure of surface roughness. It does not distinguish peaks from valleys but treats both simply as deviations from the LSQ plane. sPa is the analog of the universal roughness parameter Ra derived from a line profile, but applied to an area map.

The formula for calculating the surface roughness is described below:

The definition of average roughness of a surface (x,y) is:

$$Sa = 1/MN \Sigma\Sigma |\eta(xi, yj)|$$

(The summations are across the surface i=1 to M, j=1 to N)

M is the number of points per line and N is the number of lines. η is the deviation from the LSQ plane.

The definition is referenced in, for example, the "Manchester Report" "Development of Methods for Characterization of Roughness in Three Dimensions," p. 219, K. J. Stout, ed., Penton Press 1993. ISBN 1 8571 8023 2.

Data can be filtered using a waviness or roughness filter (essentially low and high pass filters) prior to calculation of roughness. Filters are selected based on what aspect of a surface is most important to measure (for example a speckle structure in a paint finish or longer wavelength ripples, etc.). The foam data was not filtered prior to calculation of roughness since there was no basis to do so, but a filter can be applied.

There was no filtering done to account for waviness in the samples because the samples were essentially flat over the 10 mm×10 mm area of measurement.

Foam samples with no surface texturing had surface roughness measurements of 4 μm. Similar surface roughness existed on the closed surface of hybrid absorbent foams of the invention. Lightly surface textured samples were between 40-60 μm on the open surface, and heavily textured samples were >300 μm. Good texturing is achieved at values between 40-350 μm on the open surface.

The fact that these materials have been apertured does have an impact on the surface roughness measurements, tending to increase the value somewhat. The overall impact is below 5% on the samples tested. The impact would be higher for foams with larger aperture diameters. It would be possible to get a greater than 40 μm roughness for an otherwise smooth foam if it contained a large number of apertures. Such foam would also possess acceptable texturing even though it doesn't have physical protrusions like those created by sanding, raising, or sueding.

Surfactant Permanence Test

The Surfactant Permanence Test is based upon the surface tension depression effect by surfactant addition to water. The surface tension is measured by the duNoüy ring tensiometer method utilizing a Krüss Processor Tensiometer—K 12 instrument, available from Krüss USA in Charlotte, N.C., U.S.A. In general terms, a sample of foam is soaked in distilled water and the surface tension of the supernatant is measured. This surface tension is compared to a calibration curve to determine the amount of surfactant washed from the foam.

Test preparation includes creating a calibration curve for the particular surfactant utilized. This curve shows the reduced surface tension of the solution as surfactant concentration increases. At concentrations above the critical micelle concentration (CMC), the surface tension reduction from additional surfactant is minimal.

A sample of pre-weighed foam is placed in distilled water. The sample is immersed in the room temperature water for 24 hours, allowing fugitive surfactant to leach out of the foam and dissolve into the water. The amount of water used is critical. If the amount of surfactant leached into the water creates a concentration greater than the CMC, measurement of surface tension on the solution will only indicate that the concentration is greater than the CMC. The amount of distilled water used to wash the foam is 100 times the weight of the foam. After the 24-hour soak, the foam is removed from the water/surfactant solution (supernatant). The water in the foam is allowed to drain into the supernatant and gentle pressure is applied to the foam to aid in the removal of excess supernatant in the foam. The surface tension of the total supernatant is then measured. Utilizing the calibration curve, the surface tension corresponds to a weight fraction of surfactant in the water. This weight fraction is then multiplied by the total amount of water to yield the weight of surfactant leached from the foam. The amount of surfactant removed can be expressed as a fraction of the total surfactant in the initial foam. For example: foam is made with 10 parts surfactant for every 90 parts foam. A 100 gram sample is soaked in 10,000 grams of distilled water. The surface tension measurement of the supernatant indicates that the surfactant concentration in the supernatant is 0.03%. The amount of surfactant dissolved from the foam is 3.0 grams. The amount of surfactant in the initial foam was 10 grams, so 30% of the surfactant was dissolved and 70% of the surfactant remains in the foam.

With Clariant HOSTASTAT® HS-1, the CMC is at a concentration of 0.03%, by weight. At concentrations less than the CMC, the surface tension is described by: $\sigma = 5 \ln([s]) - 18$ where σ is the surface tension and [s] is the weight fraction of the surfactant. As an example, 2.96 grams of an open-cell polystyrene foam made with 2.5 parts HOSTASTAT® HS-1 to 100 parts polystyrene was immersed in 297.79 grams of distilled water for 24 hours. The surface tension of the supernatant was measured at 39 dynes/cm which corresponds to 0.0027 grams of surfactant dissolved into the water, or 3.7% of the total surfactant; therefore, 96.3% of the surfactant remained in the foam after a 24 hour wash.

Edge Compression Test Method

The method by which the Edge-wise Compression (EC) value can be determined is set forth below. A 2-inch by 12-inch (5.1 cm by 30.5 cm) piece of absorbent foam is used. The weight of the sample is determined. The thickness of the material is measured using a hand micrometer while avoiding surface compression. The material is formed into a cylinder having a height of 2 inches (5.1 cm), and with the two ends having 0-0.125 inch (0-3.18 mm) overlap, the material is stapled together with three staples. One staple is near the middle of the width of the product, the other two nearer each edge of the width of the material. The longest dimension of the staple is in the circumference of the formed cylinder to minimize the effect of the staples on the testing.

A tensile tester, such as those commercially available from MTS Systems Corporation in Eden Prairie, Minn., U.S.A., is configured with a bottom platform, a platen larger than the circumference of the sample to be tested and parallel to the bottom platform, attached to a compression load cell placed in the inverted position. The specimen is placed on the platform under the platen. The platen is brought into contact with the specimen and compresses the sample at a rate of 25 mm./min. The maximum force obtained in compressing the sample to 50% of its width (1 inch) (2.54 cm) is recorded.

Bucking of the material is identified as a maximum in the compression force and is typically observed before the material is compressed to 50% of its uncompressed length. In a product where the length of the absorbent is less than 12 inches (30.5 cm), the EC value of the material can be determined in the following manner. Based on theoretical models governing buckling stresses, in the Edge-wise Compression configuration described, the buckling stress is proportional to $E*t^2/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force per basis weight, it can be shown that the parameter that needs to be maintained constant is $H^2/R$. Therefore, for a sample that is smaller than 12 inches (30.5 cm), the largest possible circle should be constructed and its height (width of the sample being cut out) adjusted such that $H^2/R$ equals 2.1 inches (5.3 cm). A detailed discussion of edge-wise compression strength has been given in *The Handbook Of Physical And Mechanical Testing Of Paper And Paperboard*, Richard E. Mark editor, Dekker 1983 (Vol. 1).

Vertical Wicking Fluid Flux

Definition:

The vertical wicking fluid flux is the rate of change of fluid mass that moves vertically against gravity into an absorbent material per unit of cross sectional area. In general the fluid flux changes as a function of distance from the surface of the fluid. While vertical wicking fluid flux can be defined and measured at various heights/distances from the fluid surface this testing was done at a zero height. In this way it is not necessary to measure the distance the fluid has moved as a function of time. It remains only to measure the time rate of change of fluid mass being absorbed into the sample and divide that by the cross sectional area of the material.

Figure 13:
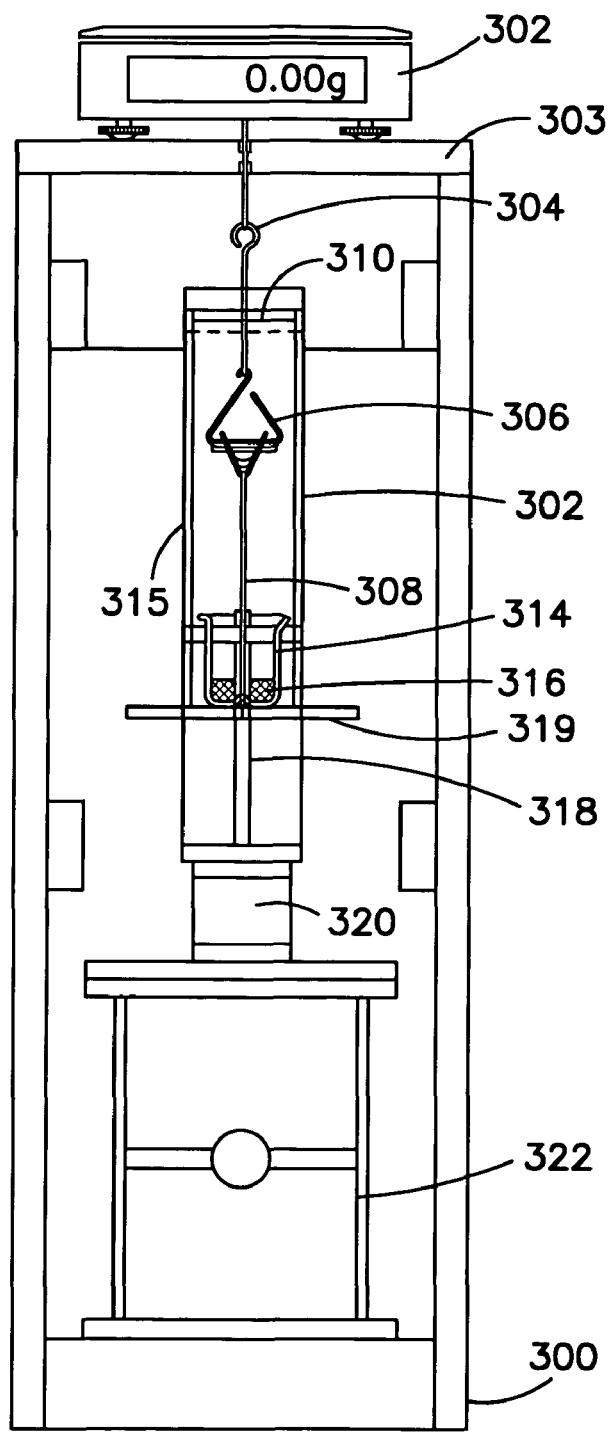
FIG. 13 schematically illustrates an apparatus used to perform the Vertical Wicking Fluid Flux Test, described herein.

Equipment: Apparatus 300 (FIG. 13) including the following:

1. Balance 302 accurate to at least 0.01 g and capable of communication with a computer. Connecting hooks 304 connect the sample holding fixture 306 to the balance 300.
2. Computer and software to record mass as a function of time accurate to 0.1 seconds.
3. Translational stage 318 capable of at least 2" vertical travel. The stage needs to move a platform 319 in the vertical direction with minimal (<1 mm) motion in the horizontal plane as the stage 318 moves. A suitable platform is 12.7 cm×12.7 cm. One electronic stage is sold by Velmex Inc. of Bloomfield, N.Y. as the translational stage model #ZMH2504W1-S2.5-FL-BK with a stepper motor and controller model VXM-1.
4. Clear acrylic tube 312. Tube is 12.7 cm OD and 5.7 cm ID. The tube should be 25.4 cm in height.
5. Tube Cover. An acrylic top that is a cylinder 1.9 cm thick with 6.35 cm outer diameter. A lip is cut so the cover fits part way into the tube. The lip is 0.64 cm deep in the thickness direction, and 0.38 cm deep in the radius direction. In the center of the cover a through hole is cut with a 0.32 cm diameter. See the drawings below.
6. Lab jack 322.

Test Method:

1. Ensure the balance 302 is aligned so that holding mechanism 306 does not touch the tube 312.
2. Cut test material to 6"×1" (15 cm×2.5 cm) strips such that the long axis is aligned with the desired direction of the fluid flow.
3. Weigh the sample. Measure the caliper of the sample to the nearest 0.05 mm with a pressure of 0.345 KPa.
4. Place sample 308 into clip in the sample holding mechanism 306.
5. Place the sample 308, the holding mechanism 306 and the sample chamber lid 310 onto the sample chamber tube 312.
6. Fill the beaker 314 with 20 ml of test fluid 316. Use 1% saline with 1 drop blue food coloring per 250 ml of fluid. Place the beaker 314 on the translational stage 318, which is controlled with a stepper motor 320.
7. Place the sample holding chamber 315 over the beaker 314 taking care not to allow the sample 318 to contact the fluid 316. If necessary adjust the sample holder 306 to get the sample 318 to be held vertically without contact with the beaker wall.
8. Connect the sample holding assembly 306 to the balance at the connecting hook.
9. Adjust the translational stage 318 and or lab jack 322 so that the sample 318 is approximately 2 mm above the surface of the fluid 316. Ensure that there is enough remaining travel in the translational stage 318 to move the beaker 314 and fluid 316 into contact with the sample 308.
10. Adjust the location of the sample chamber 315 so that the wire from the sample holder 306 is not in contact with either the vertical sample chamber lid 310 or the hole in the table 303 connecting to the wire to the balance 302.
11. Tare the balance 302.
12. Set up the computer to record the mass every second for 1800 seconds.
13. Move the translational stage 318 so the bottom edge of the sample is below the surface of the fluid by 2 mm. This must be done within 5 seconds.
14. If the sample 308 absorbs enough fluid 316 that the sample 308 is not in contact with the fluid 316 then the data is not valid. Re-run the sample so that the sample is submerged 4 mm instead of 2 mm.
15. Measure the maximum distance fluid has moved vertically, subtracting the distance the material was submerged into the fluid.
16. Measure the caliper 2 mm above the bottom edge of the sample 308. The caliper measurement should be done at 0.05 psi (0.345 KPa).

Data Analysis:

1. Using the data recorded calculate the time rate of change of fluid mass at 1000 seconds.
2. Using the sample width (2.54 cm) and the sample caliper calculate the cross sectional area.
3. Calculate the fluid flux at zero height by dividing the mass flow rate from step 1 by the cross sectional area calculated in step 2. Ensure the correct units.

It is recognized that some foams with hydration will swell and grow and therefore change in physical dimensions with fluid wicking. Significant changes in the cross-sectional area need to be accounted for in order to measure an accurate fluid flux. In addition, any significant change in the length of the foam as fluid is wicked will alter the location of the zero height position above the fluid reservoir. For these reasons, changes in the setup and test procedure may be required to accommodate such swellable foams. Such changes will be apparent to persons skilled in the art. An example of such a material is a polyurethane foam produced by Rynel Ltd., Boothbay, Me., U.S.A. and sold as RYNEL® 562-B.

The embodiments of the invention disclosed herein are exemplary. Various modifications and improvements can be made without departing from the spirit and scope of the invention. The scope of the invention is indicated by the appended claims, and all changes that fall within the meaning and range of equivalents are intended to be embraced therein.

We claim:

1. A hybrid absorbent thermoplastic foam, comprising an integrated hybrid thermoplastic foam layer having an edge region, an open surface, a closed surface and a body having a thickness defined by a distance between the open and closed surfaces;

the open surface having an open area greater than about 10%;

the body having an open-cell content of about 50% or greater;

the closed surface providing a barrier to the passage of aqueous liquids;

the body having a substantially uniform polymer composition throughout its thickness;

the hybrid absorbent foam having a bending modulus of less than 6000 KPa at 1 mm deflection, the edge region being compressed to define a seal about a periphery of the foam.

2. The hybrid absorbent foam of claim 1, wherein the body comprises an open-celled portion extending inward from the open surface, and the open-celled portion constitutes at least 50% of the thickness.

3. The hybrid absorbent foam of claim 2, wherein the open-celled portion constitutes at least 70% of the thickness.

4. The hybrid absorbent foam of claim 2, wherein the open-celled portion constitutes at least 90% of the thickness.

5. The hybrid absorbent foam of claim 2, wherein the open-celled portion constitutes at least 95% of the thickness.

6. The hybrid absorbent foam of claim 1, wherein the body has an open-cell content of about 60% or greater.

7. The hybrid absorbent foam of claim 1, wherein the body has an open-cell content of about 70% or greater.

8. The hybrid absorbent foam of claim 1, wherein the body has a density of about 0.10 grams/cm$^3$ or less, a saturated capacity of about 1 gram/gram or greater measured under a load of 3.45 KPa, and a bending modulus of less than about 6000 KPa at 1 mm deflection.

9. The hybrid absorbent foam of claim 1, wherein the polymer composition comprises at least about 45% by weight of a base resin selected from the group consisting of polystyrene, styrene copolymers, polyolefins, polyesters, biodegradable polymers, and combinations thereof.

10. The hybrid absorbent foam of claim 9, wherein the polymer composition comprises at least about 10% by weight of a thermoplastic elastomer.

11. The hybrid absorbent foam of claim 10, wherein the thermoplastic elastomer is selected from the group consisting of styrenic block copolymers including diblock and triblock copolymers of styrene-isoprene-styrene (SIS), styrene-butadiene-styrene (SBS), styrene-isoprene-butadiene-styrene (SIBS), styrene-ethylene/butylene-styrene (SEBS), styrene-ethylene/propylene-styrene (SEPS); polyolefin-based thermoplastic elastomers including random block copolymers including ethylene a-olefin copolymers; block copolymers including hydrogenated butadiene-isoprene-butadiene block copolymers; stereoblock polypropylenes; graft copolymers, including ethylene-propylene-diene terpolymer (EPDM), ethylene-propylene random copolymers (EPM) and ethylene propylene rubbers (EPR); blends of thermoplastic elastomers with dynamic vulcanized elastomer-thermoplastic blends; thermoplastic polyether ester elastomers; ionomeric thermoplastic elastomers; polyamide thermoplastic elastomers; thermoplastic polyurethanes; biodegradable polymers; and combinations thereof.

12. The hybrid absorbent foam of claim 9, wherein the polymer composition further comprises a plasticizing agent selected from the group consisting of polyethylene; ethylene vinyl acetate; mineral oil, palm oil, waxes, naphthalene oil, paraffin oil, acetyl tributyl citrate; acetyl triethyl citrate; p-tert-butylphenyl salicylate; butyl stearate; butylphthalyl butyl glycolate; dibutyl sebacate; di-(2-ethylhexyl)phthalate; diethyl phthalate; diisobutyl adipate; diisooctyl phthalate; diphenyl-2-ethylhexyl phosphate; epoxidized soybean oil; ethylphthalyl ethyl glycolate; glycerol monooleate; monoisopropyl citrate; mono-, di-, and tristearyl citrate; triactin (glycerol triacetate); triethyl citrate; 3-(2-xenoyl)-1,2-epoxypropane; and combinations thereof.

13. The hybrid absorbent foam of claim 9, wherein the polymer composition further comprises a surfactant.

14. The hybrid absorbent foam of claim 1, comprising two of the integrated hybrid foam layers.

15. The hybrid absorbent foam of claim 14, wherein the integrated hybrid foam layers are joined at their respective closed surfaces.

16. The hybrid absorbent foam of claim 1, wherein the open surface has a surface roughness of about 40 to about 350 microns.

17. The hybrid absorbent foam of claim 1, wherein the compressed edge region comprises thermal bonds.

18. An absorbent article, comprising at least two integrated hybrid thermoplastic foam layers, each of the integrated hybrid thermoplastic foam layers having an edge region, an open surface, a closed surface, and a body having a thickness defined by a distance between the open and closed surfaces;

the open surface having an open area greater than about 10%;

the body having an open-cell content of about 50% or greater;

the closed surface providing a barrier to the passage of aqueous liquids;

the body having a substantially uniform polymer composition throughout its thickness;

the integrated hybrid foam layer having a bending modulus of less than 6000 KPa at 1 mm deflection, the integrated hybrid foam layers being joined together about at least a portion of their edge regions with their respective closed surfaces facing each other to define an open space therebetween.

19. The absorbent article of claim 18, wherein the article comprises a personal care absorbent article.

20. The absorbent article of claim 18, wherein the article comprises a medical absorbent article.

21. The absorbent article of claim 18, wherein the article comprises an industrial absorbent article.

22. The absorbent article of claim 18, wherein the article comprises a glove or mitt.

23. The absorbent article of claim 18, wherein the open surface and a portion of the body are apertured and the closed surface is not apertured.

24. The absorbent article of claim 23, wherein the article is a wipe.

25. The absorbent article of claim 24, wherein each of the integrated hybrid thermoplastic foam layers has compressed edge regions.

26. The absorbent article of claim 18, wherein the article is a stack of wipes comprising a plurality of wipes superimposed on one another, and each of the wipes comprises at least one of the integrated hybrid foam layers.

27. The absorbent article of claim 26, wherein the wipes are peelably bonded together.

28. The absorbent article of claim 18, comprising a roll of the integrated hybrid foam layer.

29. The absorbent article of claim 18, wherein at least one of the integrated hybrid thermoplastic foam layers is pre-saturated with a deliverable fluid.

30. The absorbent article of claim 29, wherein the deliverable fluid is a cleaning fluid.

31. The absorbent article of claim 29, wherein the deliverable fluid is a lotion.

32. The absorbent article of claim 18, wherein the open surface has a surface roughness of about 40 to about 350 microns.

* * * * *